United States Patent
Sharma et al.

(10) Patent No.: US 8,835,711 B2
(45) Date of Patent: Sep. 16, 2014

(54) ANF-RGC IN-GENE KNOCK-OUT ANIMAL

(75) Inventors: Rameshwar K. Sharma, Maple Glen, PA (US); Teresa Duda, Horsham, PA (US)

(73) Assignee: Salus University, Elkins Park, PA (US)

( * ) Notice: Subject to any disclaimer, the term of this patent is extended or adjusted under 35 U.S.C. 154(b) by 0 days.

(21) Appl. No.: 13/476,305

(22) Filed: May 21, 2012

(65) Prior Publication Data

US 2013/0291132 A1 Oct. 31, 2013

Related U.S. Application Data

(60) Provisional application No. 61/639,183, filed on Apr. 27, 2012.

(51) Int. Cl.
*A01K 67/027* (2006.01)
*C12N 15/85* (2006.01)

(52) U.S. Cl.
USPC ............................................ 800/18; 435/325

(58) Field of Classification Search
None
See application file for complete search history.

(56) References Cited

PUBLICATIONS

Sigmund, C.D. 2000. Arterioscler Thromb Vasc Biol.20:1425-1429.*
Wall, R.J. 1996. Theriogenology 45:57-68.*
Mullins et al. (1996, Clin. Invest. vol. 97, No. 7, 1557-1560.*
Bradley et al. Biotechnology, vol. 10, 1992. pp. 534-539.*
Campbell and Wilmut, Theriogenology, vol. 47. pp. 63-69, 1997.*
R. K. Sharma, et al., "Allosteric regulatory step and configuration of the ATP-binding pocket in atrial natriuretic factor receptor guanylate cyclase transduction mechanism," Can J. Physiol Pharmacol 79, pp. 682-691. (2001) US.
A. K. Paul; et al., "Coexistence of guanylate cyclase and atrial natriuretic factor receptor in a 180-kD protein," Science 240: pp. 805-806. (1987) US.
R. K. Sharma, "Membrane guanylate cyclase is a beautiful signal transduction machine: overview," Mol Cell Biochem 334: pp. 3-36, (2010) US.
T. Duda, et al., "Site-directed mutational analysis of a membrane guanylate cyclase cDNA reveals the atrial natriuretic factor signaling site," Proc Natl Acad Sci U S A 88, pp. 7882-7886. (1991) US.
T. Duda, et al., "ATP regulated module (ARM) of the atrial natriuretic factor receptor guanylate cyclase," Peptides 26: pp. 969-984. (2005) US.
T. Duda, et al., "Atrial natriuretic factor receptor guanylate cyclase signaling: new ATP-regulated transduction motif," Mol Cell Biochem 324, pp. 39-53. (2009) US.
Goraczniak RM, Duda T, Sharma RK, "A structural motif that defines the ATP-regulatory module of guanylate cyclase in atrial natriuretic factor signalling," Biochem J 282, 533-537 (1992) US.
Marala R, Duda T, Goraczniak RM, Sharma RK. Genetically tailored atrial natriuretic factor-dependent guanylate cyclase. Immunological and functional identity with 180 kDa membrane guanylate cyclase and ATP signaling site. FEBS Lett 296, 254-258 (1992) US.
Duda T, Goraczniak RM, Sharma RK. Core sequence of ATP regulatory module in receptor guanylate cyclases. FEBS Lett 315, 143-148 (1993) US.
Duda T, Yadav P, Sharma RK. ATP allosteric activation of atrial natriuretic factor receptor guanylate cyclase. FEBS J 277, 2550-2563 (2010) US.
Duda T, Yadav P, Sharma RK. Allosteric modification, the primary ATP activation mechanism of atrial natriuretic factor receptor guanylate cyclase. Biochemistry 50, 1213-1225 (2011) US.
Duda T, Pertzev A, Sharma RK. "The ANF-RGC Gene Motif WTAPELL is Vital for Blood Pressure Regulation: Biochemical Mechanism," Biochemistry 52, pp. 2337-2347 (2013) US.
Pandey K. "Guanylyl Cyclase/Atrial Natriuretic Peptide Receptor-A: Role in the Pathophysiology of Cardiovascular Regulation," Can J. Physiol Pharmacol 89(8), pp. 557-573 (2011) US.
Tsai E, Kass D. "Cyclic GMP Signaling in Cardiovascular Pathophysiology and Therapeutics," Pharmacol Ther 122 (3), pp. 216-238 (2009) US.

* cited by examiner

*Primary Examiner* — Celine Qian
(74) *Attorney, Agent, or Firm* — J. Eric Sumner

(57) ABSTRACT

The present invention relates to transgenic animals comprising a mutation or deletion to the ANF-RGC protein, particularly to its ARM and/or its ATS-ST region. Such animals may be used to study the effects on pathways associated with ANF-RGC activation, including, but not limited to, hypertension. Such animals may also be used in drug screen assays, to establish toxicity profiles, or other similar methods discussed herein known in the art.

13 Claims, 5 Drawing Sheets

ANF-RGC IN-GENE KNOCK-OUT ANIMAL

STATEMENT REGARDING FEDERALLY SPONSORED RESEARCH OR DEVELOPMENT

This invention was made with partial Government support under Grant Number S82701 awarded by the National Institutes of Health (NIH). The Government has certain rights in this invention.

FIELD OF THE INVENTION

The present invention relates to transgenic animals having a mutation or deletion to the ANF-RGC protein, particularly to its ARM and/or ATP-ST region, and to methods of using such animals.

BACKGROUND OF THE INVENTION

More than 74 million American adults have hypertension, or high blood pressure, which has no noticeable symptoms but results in greater risk for stroke, heart attack, or other heart damage. Membrane bound Atrial Natriuretic Factor Receptor Guanylate Cyclase (ANF-RGC) is one of the major physiological regulators of cardiovascular and renal homeostasis and, in particular, has been linked with blood pressure regulation. It acts as the surface receptor of the two natriuretic peptide hormones, atrial natriuretic factor (ANF) and B-type natriuretic peptide (BNP). Upon binding of these hormones, ANF-RGC initiates a cascade of structural changes, ultimately transmitted through the transmembrane domain to the intracellular portion of the protein. At the C-terminal catalytic domain, it is translated into the generation of cyclic GMP. Cyclic GMP then serves as the second messenger for downstream control of cardiovascular and renal homeostasis, including relaxation of blood vessels and cardiac smooth muscle and decreasing blood pressure.

ANF-RGC machinery and its response to ANF/BNP-ligand stimulation is complex and requires co-binding of both the extracellular ligand (e.g. ANF or BNP) and intracellular ATP. The binding of both causes allosteric modifications of the ANF-RGC protein that ultimately leads to activation of its catalytic domain. An ATP-signal transmitting motif, ATP-ST, is critical for the transduction of the ANF (or BNP) and ATP signals into the production of the cyclic GMP. The ATP-ST constitutes a 7-amino acid motif spanning amino acids 669-675 of the ANF-RGC protein and is contained within the ATP-regulated module (ARM) of the ANF-RGC protein. It controls almost all (~95%) of the total stimulated activity of ANF-RGC, i.e. cyclic GMP production.

Accordingly, the ANF-RGC protein, particularly the ARM and ATP-ST domain, presents an attractive target for studying the ANF-RGC-mediated cyclic GMP pathway and its effects on cardiovascular and/or renal homeostasis. It also presents an attractive target for potential therapeutic agents for treating diseases or disorders associated with the ANF-RGC-mediated cyclic GMP pathway, such as, but not limited to, hypertension.

SUMMARY OF THE INVENTION

In one aspect, the present invention relates to a transgenic animal whose genome includes a mutation or deletion to the ARM portion of the ANF-RGC protein. The mutation or deletion may be to a region or regions of the ARM portion that contribute, in whole or part, to the ANF-RGC production of cyclic GMP. To this end, and in certain embodiments, the mutation or deletion affects or diminishes the ability of the ANF-RGC protein to produce cyclic GMP. In certain embodiments the mutation or deletion is to one or a combination of the following positions of the ARM region: $^{669}$TrpThrAlaProGluLeuLeu$^{675}$ (SEQ ID NO.: 3), $^{631}$SerSerAsnCysValValAspGlyArg$^{639}$ (SEQ ID NO.: 15), $^{503}$GlyArgGlySerAsnTyrGly$^{509}$ (SEQ ID NO.: 16), $^{642}$ValLysIleGlyAspPheGlyMet$^{649}$ (SEQ ID NO.: 17), lysine$^{535}$, glutamate$^{555}$, and aspartate$^{646}$. In further aspects, the mutation or deletion is to the ATP-ST region of the ARM portion, which includes amino acid residues 669 through 675 of the ANF-RGC protein and is provided herein as SEQ ID NO.: 3. This mutation may include a deletion of a portion of or the entire ATP-ST region. The mutation or deletion to this region or any of the regions herein may be heterozygous or homozygous in the transgenic animal.

The transgenic animals of the present invention may exhibit one or more of the following phenotypic traits associated with ANF-RGC mutation. In one aspect, the transgenic animal exhibits reduced ligand-stimulated guanylate cyclase activity, as defined herein and as compared to an animal with the wildtype gene. While not limited thereto, in certain aspects, the reduced ligand-stimulated guanylate cyclase activity is observed in at least the tissue or cells of the heart, kidney, and/or adrenal gland. In further aspects, the transgenic animal exhibits renal or cardiac cell hypertrophy, as compared to a mouse having a wildtype genome. One or more of the foregoing changes may result in an animal model having reduced cyclic GMP production and/or exhibiting hypertension or high blood pressure. In even further aspects, the transgenic animal exhibits no change in basal guanylate cyclase activity, as defined herein.

The transgenic animals of the present invention may be used in one or more methods provided herein, particularly, though not exclusively, associated with the study of the ANF-RGC pathway or a drug or therapeutic screening assay. In one example, the transgenic animal may be used to test the effects of an anti-hypertension drug or therapeutic targeting a protein or enzyme other than ANF-RGC. To this end, the drug or therapeutic is provided to the transgenic animal, and the animal is measured for a decrease of blood pressure, wherein a decrease in blood pressure indicates that the drug or therapeutic is effective.

In a further method, the transgenic animals of the present invention may be used to establish a toxicity profile of a hypertension therapeutic. To this end, a drug or therapeutic is provided to the animal, where the drug or therapeutic may be designed to modulate ANF-RGC activity. The animal is then measured for a change in a level of at least one component other than ANF-RGC (e.g. mRNA expression levels of other proteins) in response to the administration of the drug or therapeutic relative to the transgenic mouse not exposed to the drug or agent. A change in level of at least one component indicates a potential side-effect of the drug of therapeutic.

In even further embodiments, the transgenic animals of the present invention may be used to control expression of ANF-RGC. To this end, cells of the transgenic animals are transfected with a vector encoding ANF-RGC, where the promoter region of the vector is adapted to control expression rates in a tissue. In certain instances the promoter region is adapted for high or constitutive expression levels in a targeted tissue type, such as heart tissue, renal tissue, or adrenal tissue. Such transfected animals may be used to study the effects of ANF-RGC over-expression in such cells/tissue or otherwise as a drug screen tool for a drug or therapeutic targeting ANF-RGC activity.

One of skill in the art will readily appreciate that the foregoing is not necessarily limiting to the invention and that additional embodiments and advantages of the present invention are readily available based on the disclosure provided herein.

To aid in the understanding of the invention, the following non-limiting definitions are provided:

The term "ANF-RGC" refers to the protein Atrial Natriuretic Factor Receptor Guanylate Cyclase in its membrane-bound or soluble form. The DNA and amino acid sequences of the rat protein are provided in SEQ ID NOS.: 1 and 2, respectively. The DNA and amino acid sequences of the mouse protein are provided in SEQ ID NOS.: 4 and 5, respectively. The definition of this term is not limited to such sequences, however, and may also include the human form of the protein or any other allelic, species and induced variants thereof. Induced variants preferably show at least 90%, 95% or 99% sequence identity at the nucleic acid or amino acid sequences above.

The terms "alter" or "diminish," as it pertains to the activity of ANF-RGC in the mutated form, refers to ANF-RGC having decreased activity, as compared to the wildtype, or having little or no ANF-RGC activity. In certain aspects, such diminished activity results in a decrease in cyclic GMP production, an increase in cell hypertrophy (particularly cells from heart, renal or adrenal tissue), or any of the other phenotypic traits discussed herein.

As used herein, "animal" includes all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule, in the case of the present invention an altered ANF-RGC gene. This molecule may be specifically targeted to defined genetic locus, be randomly integrated within a chromosome, or it may be extra-chromosomally replicating DNA.

As used herein the term, "selection marker" means a gene product which may be selected for or against using chemical compounds. Selection markers often are enzymes with an ability to metabolize the toxic drugs into non-lethal products. For example, the pac (puromycin acetyl transferase) gene product can metabolize puromycin, the dhfr gene product can metabolize trimethoprim (tmp) and the bla gene product can metabolize ampicillin (amp). Selectable markers may convert a benign drug into a toxin. For example, the HSV tk gene product can change its substrate, FIAU, into a lethal substance. A preferred selection marker is one which may be utilized in both prokaryotic and eukaryotic cells. The neo gene, for example, metabolizes and neutralizes the toxic effects of the prokaryotic drug, kanamycin, as well as the eukaryotic drug, G418.

BRIEF DESCRIPTION OF THE FIGURES

Figure 4:
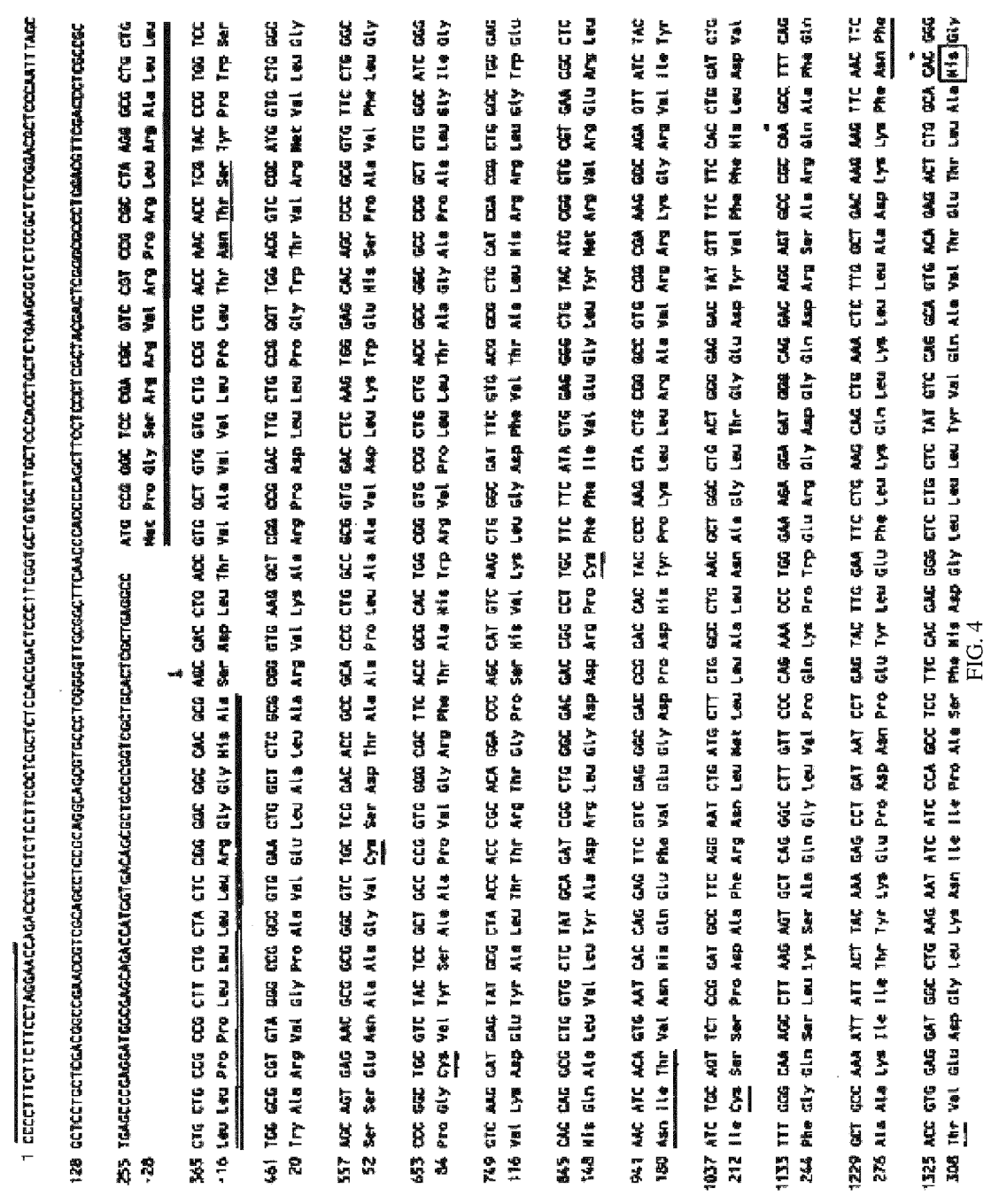

FIG. 4 provides the nucleotide and deduced amino acid sequence of the rat ANF-RGC determined in the applicant's laboratory.

DETAILED DESCRIPTION OF THE INVENTION

Figure 1:
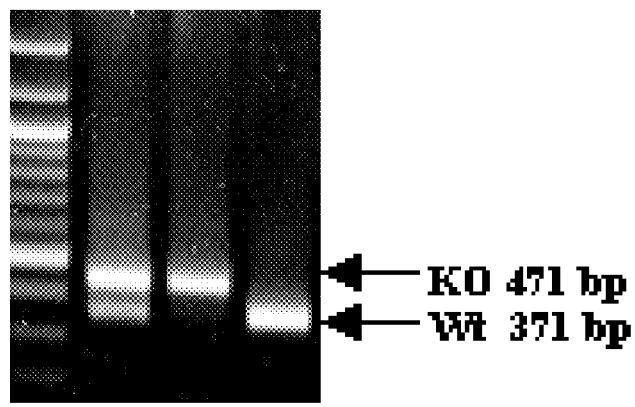
FIG. 1 illustrates an agarose gel showing genotyping for WTAPELL deletion mouse model; the expected band for ($^{669}$WTAPELL$^{675}$)$^{-/-}$ is 471 bp and for wt 371 bp.

In certain aspects, the present invention provides a transgenic animal deficient in at least one functional allele encoding ANF-RGC. Though not necessarily limiting to the invention, the deficiency results in a diminished activity of the expressed ANF-RGC protein, in particular a diminished ability of the expressed ANF-RGC protein to generate cyclic GMP. In further aspects, the deficiency may also, or alternatively, result in phenotypic traits such as, but not limited to, tissue hypertrophy, hypertension, and the like. Such an animal may be used to study the effects of such a deficiency on the ANF-RCG-mediated pathway or as a drug screening tool for diseases or disorders associated with ANF-RCG, hypertension, or the like.

As used herein, the term "ANF-RGC" refers to any form of the ANF-RGC gene or protein. In certain aspects, it refers to the rat, murine, or human form of the gene, which have a nucleic acid sequence and amino acid sequence, as follows:

Rat ANF-RGC cDNA (SEQ ID NO.: 1)
```
ATGCCGGGCTCCCGACGCGTCCGTCCGCGCCTAAGGGCGCTGCTGCTGCTGCCGCCGCTTCTGCTACTCCGGGGCGGCCACGCGAGC
GACCTGACCGTGGCTGTGGTGCTGCCGCTGACCAACACCTCGTACCCGTGGTCCTGGGCGCGTGTAGGGCCGGCCGTGGAACTGGCT
CTCGCGCGGGTGAAGGCTCGGCCGGACTTGCTGCCGGGTTGGACGGTCCGCATGGTGCTGGGCAGCAGTGAGAACGCGGCGGGCGTC
TGCTCGGACACCGCCGCCACCGCTGGCCGCGGTGGACCTCAAGTGGGAGCACAGCCCCGCGGTGTTCCTGGGCCCCGGCTGCGTCTAC
TCCGCTGCCCCGGTGGGGCGCTTCACCGCGCACTGGCGGGTGCCGCTGCTGACCGCCGGCGCCCCGGCTCTGGGCATCGGGGTCAAG
GATGAGTATGCGCTAACCACCCGCACAGGACCCAGCCATGTCAAGCTGGGCGATTTCGTGACGGCGCTGCATCGACGGCTGGGCTGG
GAGCACCAGGCGCTGGTGCTCTATGCAGATCGGCTGGGCGACGACCGGCCTTGCTTCTTCATAGTGGAGGGGCTGTACATGCGGGTG
CGTGAACGCCTCAACATCACAGTGAATCACCAGGAGTTCGTCGAGGGCGACCCGGACCACTACCCCAAGCTACTGCGGGCCGTGCGG
CGAAAGGGCAGAGTTATCTACATCTGCAGTTCTCCGGATGCCTTCAGGAATCTGATGCTTCTGGCCCTGAACGCTGGCCTGACTGGG
GAGGACTATGTTTCTTCCACCTGGATGTGTTTGGGCAAAGCCTTAAGAGTGCTCAGGGCCTTGTTCCCCAGAAACCCTGGGAAAGA
GGAGATGGGCAGGACAGGAGTGCCCGCCAAGCCTTTCAGGCTGCCAAAATTATTACTTACAAAGAGCCTGATAATCCTGAGTACTTG
GAATTCCTGAAGCAGCTGAAACTCTTGGCTGACAAGAAGTTCAACTTCACCGTGGAGGATGGCCTGAAGAATATCATCCCAGCCTCC
TTCCACGACGGGCTCCTGCTCTATGTCCAGGCAGTGACAGGACTCTGGCACACGGGGACATGTCACAGATGGAGAGAACATCACT
CAGCGGATGTGGAACCGAAGCTTCCAAGGTGTGACAGGATACCCGAAAATTGATAGAAACGGAGATCGGGACACCGATTTCTCTCTC
TGGGATATGGATCCAGAGACGGGTGCCTTCAGGGTTGTCCTGAACTATAATGGTACTTCCCAGGAGCTAATGGCTGTGTCAGAACAC
AAATTATACTGGCCTCTGGGATATCCACCTCCTGACGTCCCTAAATGTGGCTTTGACAATGAGGACCCAGCCTGCAACCAAGACCAC
TTTTCCACACTGGAGGTTCTGGCTTTGGTGGGCAGCCTCTCTCTGATTAGCTTTCTGATTGTGTCTTTCTTCATATACAGGAAGATG
CAGCTGGAAAAGGAGCTGGTCTCAGAGTTGTGGCGGGTGCGCTGGGAGGACTTGCAGCCCAGCAGCCTGGAGAGGCACCTTCGGAGC
GCTGGCAGCCGGCTGACCCTGAGTGGGCGAGGCTCCAATTATGGCTCCCTGCTAACCACCGAGGGCCAGTTCCAAGTCTTTGCCAAG
```

-continued

```
ACAGCATACTATAAGGGCAACCTTGTGGCTGTGAAACGTGTGAACCGGAAACGCATTGAGTTGACACGAAAAGTCCTGTTTGAACTT
AAACATATGCGGGATGTGCAGAATGACCACTTGACAAGATTTGTGGGTGCTTGTACCGACCCCCCCAACATCTGTATCCTCACAGAG
TACTGTCCCCGTGGAAGCCTACAGGACATTCTAGAGAATGAGAGTATCACCCTGGACTGGATGTTTCGGTACTCGCTCACCAATGAC
ATTGTCAAGGGAATGCTCTTTCTACACAATGGGGCCATTTGTTCCCATGGGAACCTCAAGTCATCCAACTGTGTGGTAGACGGGCGC
TTCGTGTTAAAGATCACAGACTACGGTCTTGAGAGCTTCAGAGACCCGGAGCCAGGACCAGGGACCACCCCTCTTTGCCAAAAAATTG
TGGACGGCACCTGAGCTCCTGCGAATGGCTTCGCCACCTGCCCGTGGCTCCCAAGCTGGGGATGTGTACAGCTTTGGTATCATCCTG
CAGGAGATTGCCCTAAGAAGTGGGGTCTTCTATGTGGAAGGTTTGGACCTCAGCCCAAAAGAGATCATTGAGCGTGTGACTCGGGGT
GAGCAGCCCCCATTCCGACCCTCCATGGATCTGCAGAGCCACCTGGAGGAACTGGGGCAGCTGATGCAGCGGTGCTGGGCAGAGGAC
CCACAGGAGCGGCCACCCTTTCAGCAGATCCGCCTGGCGCTGAGGAAGTTCAACAAGGAGAACAGCAGCAACATCCTGGACAACCTG
CTGTCACGCATGGAGCAGTATGCTAACAACCTGGAGGAACTGGTAGAGGAGAACACAAGCTTATCTGGAGGAGAAGCGCAAAGCT
GAGGCCTTGCTTTACCAGATTCTGCCTCACTCCGTGGCTGAGCAGCTGAAGAGAGGCGAGACAGTCCAGGCTGAGGCCTTTGATAGT
GTTACCATCTACTTCAGTGATATTGTGGGCTTTACAGCTCTTTCAGCAGAAAGCACACCCATGCAGGTGGTGACTCTGCTCAATGAT
CTGTACACCTGTTTTGATGCTGTCATAGACAACTTTGATGTGTACAAGGTGGAGACCATTGGTGATGCTTACATGGTGGTGTCAGGG
CTCCCAGTGCGGAATGGACAACTCCACGCCCGAGAGGTGGCCCGAATGGCACTTGCACTACTGGATGCTGTGCGCTCCTTCCGCATC
CGCCATAGGCCCCAGGAACAGCTGCGCTTGCGCATTGGCATCCACACAGGTCCTGTGTGTGCTGGTGTGGTAGGGCTAAAGATGCCC
CGATACTGCCTCTTTGGAGACACAGTCAACACAGCTTCAAGAATGGAGTCTAATGGAGAAGCCCTCAAGATCCACTTGTCTTCTGGA
CAGAGACCAAGGCTGTGAGAGTTCGATGGTTTCGAGCTGGAGCTCCGAGGGGATGTGGAAATGAAGGGCAAAGGCAAGGTTCGGACC
TATTGGCTCCTGGGGGAGCGGGGATGTAGCACTCGAGGC
```

Rat ANF-RGC amino acid sequence (SEQ ID NO.: 2)

```
Met Pro Gly Ser Arg Arg Val Arg Pro Arg Leu Arg Ala Leu Leu Leu Leu Pro Pro Leu Leu Leu
Leu Arg Gly Gly His Ala Ser Asp Leu Thr Val Ala Val Val Leu Pro Leu Thr Asn Thr Ser Tyr
Pro Trp Ser Try Ala Arg Val Gly Pro Ala Val Glu Leu Ala Leu Ala Arg Val Lys Ala Arg Pro
Asp Leu Leu Pro Gly Trp Thr Val Arg Met Val Leu Gly Ser Ser Glu Asn Ala Ala Gly Val Cys
Ser Asp Thr Ala Pro Leu Ala Val Asp Leu Lys Trp Glu His Ser Pro Ala Val Phe Leu
Gly Pro Gly Cys Val Tyr Ser Ala Ala Pro Val Gly Arg Phe Thr Ala His Trp Arg Val Pro Leu
Leu Thr Ala Gly Ala Pro Ala Leu Gly Ile Gly Val Lys Asp Glu Tyr Ala Leu Thr Thr Arg Thr
Gly Pro Ser His Val Lys Leu Gly Asp Phe Val Thr Ala Leu His Arg Arg Leu Gly Trp Glu His
Gln Ala Leu Val Leu Tyr Ala Asp Arg Leu Gly Asp Arg Pro Cys Phe Phe Ile Val Glu Gly
Leu Tyr Met Arg Val Arg Glu Arg Leu Asn Ile Thr Val Asn His Gln Glu Phe Val Glu Gly Asp
Pro Asp His Tyr Pro Lys Leu Leu Arg Ala Val Arg Arg Lys Gly Arg Val Ile Tyr Ile Cys Ser
Ser Pro Asp Ala Phe Arg Asn Leu Met Leu Leu Ala Leu Asn Ala Gly Leu Thr Gly Glu Asp Tyr
Val Phe Phe His Leu Asp Val Phe Gly Gln Ser Leu Lys Ser Ala Gln Gly Leu Val Pro Gln Lys
Pro Trp Glu Arg Gly Asp Gly Gln Asp Arg Ser Ala Arg Gln Ala Phe Gln Ala Ala Lys Ile Ile
Thr Tyr Lys Glu Pro Asp Asn Pro Glu Tyr Leu Glu Phe Leu Lys Gln Leu Lys Leu Leu Ala Asp
Lys Lys Phe Asn Phe Thr Val Glu Asp Gly Leu Lys Asn Ile Ile Pro Ala Ser Phe His Asp Gly
Leu Leu Leu Tyr Val Gln Ala Val Thr Glu Thr Leu Ala His Gly Gly Thr Val Thr Asp Gly Glu
Asn Ile Thr Gln Arg Met Trp Asn Arg Ser Phe Gln Gly Val Thr Gly Tyr Pro Lys Ile Ser Arg
Asn Gly Asp Arg Asp Thr Asp Phe Ser Leu Trp Asp Met Asp Pro Glu Thr Gly Ala Phe Arg Val
Val Leu Asn Tyr Asn Gly Thr Ser Gln Glu Leu Met Ala Val Ser Glu His Lys Leu Tyr Trp Pro
Leu Gly Tyr Pro Pro Pro Asp Val Pro Lys Cys Gly Phe Asp Asn Glu Asp Pro Ala Cys Asn Gln
Asp His Phe Ser Thr Leu Glu Val Leu Ala Leu Val Gly Ser Leu Ile Ser Pro Phe Leu Ile
Val Ser Phe Phe Ile Tyr Arg Lys Met Gln Leu Glu Lys Glu Leu Val Ser Glu Leu Trp Arg Val
Arg Trp Glu Asp Leu Gln Pro Ser Ser Leu Glu Arg His Leu Arg Ser Ala Gly Ser Arg Leu Thr
Leu Ser Gly Arg Gly Ser Asn Tyr Gly Ser Leu Leu Thr Thr Glu Gly Gln Phe Gln Val Phe Ala
Lys Thr Ala Tyr Tyr Lys Gly Asn Leu Val Ala Val Lys Arg Val Asn Arg Lys Arg Ile Glu Leu
Thr Arg Lys Val Leu Phe Glu Leu Lys His Met Arg Asp Val Gln Asn Glu His Leu Thr Arg Phe
Val Gly Ala Cys Thr Asp Pro Pro Asn Ile Cys Ile Leu Thr Glu Tyr Cys Pro Arg Gly Ser Leu
Gln Asp Ile Leu Glu Asn Glu Ser Ile Thr Leu Asp Trp Met Phe Arg Tyr Ser Leu Thr Asn Asp
Ile Val Lys Gly Met Leu Phe Leu His Asn Gly Ala Ile Cys Ser His Gly Asn Leu Lys Ser Ser
Asn Cys Val Val Asp Gly Arg Phe Val Leu Lys Ile Thr Asp Tyr Gly Leu Glu Ser Phe Arg Asp
Pro Glu Pro Glu Gln Gly His Thr Leu Phe Ala Lys Lys Leu Trp Thr Ala Pro Glu Leu Leu Arg
Met Ala Ser Pro Pro Ala Arg Gly Ser Gin Ala Gly Asp Val Tyr Ser Phe Gly Ile Ile Leu Gln
Glu Ile Ala Leu Arg Ser Gly Val Phe Tyr Val Gly Gly Leu Ser Pro Lys Glu Ile Ile
Glu Arg Val Thr Arg Gly Glu Gln Pro Pro Phe Arg Pro Ser Met Asp Leu Gln Ser His Leu Glu
Glu Leu Gly Gln Leu Met Gln Arg Cys Trp Ala Glu Asp Pro Gln Glu Arg Pro Pro Phe Gln Gln
Ile Arg Leu Ala Leu Arg Lys Phe Asn Lys Glu Asn Ser Ser Asn Ile Leu Asp Asn Leu Leu Ser
Arg Met Glu Gln Tyr Ala Asn Asn Leu Glu Glu Leu Val Glu Glu Arg Thr Gln Leu Tyr Leu Glu
Glu Lys Arg Lys Ala Glu Ala Leu Leu Tyr Gln Ile Leu Pro His Ser Val Ala Glu Gln Leu Lys
Arg Gly Glu Thr Val Gln Ala Glu Ala Phe Asp Ser Val Thr Ile Tyr Phe Ser Asp Ile Val Gly
Phe Thr Ala Leu Ser Ala Glu Ser Thr Pro Met Gln Val Val Thr Leu Leu Asn Asp Leu Tyr Thr
Cys Phe Asp Ala Val Ile Asp Asn Phe Asp Val Tyr Lys Val Glu Thr Ile Gly Asp Ala Tyr Met
Val Val Ser Gly Leu Pro Val Arg Asn Gly Gln Leu His Ala Glu Val Ala Arg Met Ala Leu
Ala Leu Leu Asp Ala Val Arg Ser Phe Arg Ile Arg His Arg Pro Gln Glu Gln Leu Arg Leu Arg
Ile Gly Ile His Thr Gly Pro Val Cys Ala Gly Val Val Gly Leu Lys Met Pro Arg Tyr Cys Leu
Phe Gly Asp Thr Val Asn Thr Ala Ser Arg Met Glu Ser Asn Gly Glu Ala Leu Lys Ile His Leu
Ser Ser Glu Thr Lys Ala Val Leu Glu Glu Phe Asp Gly Phe Glu Leu Glu Leu Arg Gly Asp Val
Glu Met Lys Gly Lys Gly Lys Val Arg Thr Tyr Trp Leu Leu Gly Glu Arg Gly Cys Ser Thr Arg
Gly
```

Mouse ANF-RGC cDNA (SEQ ID NO.: 4)

```
ATGCCGCGTTCCCGACGCGTCCGTCCGCGCCTAAGGGCGCTGCTGCTGCTACCGCCGCTGCTGCTGCTCCGAAGCGGCCACGCGAGC
GACCTGACCGTGGCTGTGGTGCTGCCCGTGACCAACACCTCGTACCCGTGGTCCTGGGCGCGTGTAGGGCCGGCGGTGGAACTGGCT
CTCGGGAGGGTGAAGGCTCGGCCGGACTTGCTGCCGGGTTGGACGGTCCGTATGGTGCTGGGCAGCAGCGAGAACGCGGCGGGCGTC
TGCTCCGACACCGCTGCACCGCTGGCCGCGGTGGATCTCAAGTGGGAGCACAGCCCGGCGGTCTTCCTGGGCCCGGCTGCGTATAC
TCTGCTGCCCCGGTGGACCGCTTCACCGCGCACTGGCGGTTGCCGCTGCTGACGGCTGGCCCCGGCTCTGGGCATCGGGGTGAAG
GATGAGTACGCGTTAACCACCCGCACAGGACCCAGCCATGTCAAGCTGGGCGACTTCGTGACGGCGCTGCATCGACGGCTGGGCTGG
GAGCACCAGGCGCTTGTGCTCTATGCAGATCGGCTGGGCGACGACCGGCCGTGCTTCTTCATAGTGGAGGGGCTGTACATGCGGGTG
CGTGAGCGACTCAACATCACAGTAAATCACCAGGAGTTCGTCGAGGGCGACCCGGACCACTACACCAAGCTACTGCGGACCGTGCAG
```

-continued

```
CGCAAGGGCAGAGTTATCTACATCTGCAGTTCTCCGGATGCCTTCAGGAATCTGATGCTTTTGGCCCTGGATGCTGGCCTGACTGGG
GAGGACTATGTTTTCTTCCACCTGGATGTGTTTGGGCAAAGCCTTCAGGGTGCTCAGGGCCCTGTTCCAGAGAAGCCCTGGGAAAGA
GACGATGGGCAGGATAGGAGAGCCCGCCAGCGCTTTCAGGCTGCAAAAATTATTACTTACAAAGAACCCGATAATCCTGAGTACTTG
GAATTCCTGAAGCAGCTAAAACTCTTGGCTGACAAGAAATTCAACTTCACCATGGAGGATGGCCTGAAAAATATCATCCCAGCATCC
TTCCATGACGGGCTCCTGCTCTATGTCCAGGCAGTGACAGAGACTCTGGCACAGGGGGGCACTGTCACTGATGGAGAGAACATCACT
CAGCGGGATGTGGAACCGAAGCTTCCAAGGTGTGACAGGATACCTGAAATTGATAGAAATGGAGATCGGACACTGATTCTCCTCTC
TGGGATATGGACCCCGAGACAGGTGCCTTCAGGGTTGTCCTGAACTTTAATGGTACTTCCCAGGAGCTGATGGCTGTGTCAGAACAC
AGATTATACTGGCCTCTGGGATACCCACCTCCTGACATCCCTAAATGTGGCTTTGACAATGAGGACCCAGCCTGCAACCAAGACCAC
TTTTCCACACTGGAGGTTCTGGCTTTGGTGGGCAGCCTCTCTCTGGTTAGCTTTCTGATCGTGTCTTTCTTCATATACAGGAAGATG
CAGCTGGAAAAGGAGCTGGTCTCAGAGTTGTGGCGGGTGCGCTGGGAGGACTTGCAGCCCAGCAGCCTGGAGAGGCACCTTCGGAGC
GCTGGCAGTCGGCTGACCCTGAGTGGGCGAGGCTCCAATTATGGCTCCCTGCTAACCACGGAGGGCCAGTTCCAAGTCTTTGCCAAG
ACAGCATACTATAAGGGCAACCTCGTGGCTGTGAAACGTGTGAACCGGAAACGCATTGAGTTGACACGAAAAGTCCTGTTTGAACTT
AAACATATGCGGGATGTGCAGAATGAGCAATTGACCAGATTTGTGGGAGCTTGTACCGACCCTCCCAACATCTGTATCCTCACAGAG
TACTGTCCCCGTGGAAGCCTACAGGACATTCTAGAGAATGAGAGTATTACCCTGGACTGGATGTTTCGGTACTCACTCACCAATGAC
ATTGTCAAGGGAATGCTCTTTCTACAACGGGGCCATTTGTTCCCATGGGAACCTCAAGTCATCCAACTGCGTGGTAGATGGACGT
TTTGTGTTAAAGATCACAGACTATGGGCTCGAGAGCTTCAGAGACCCGGAGCCAGAGCAAGGACACACCCTCTTTGCCAAAAACTG
TGGACTGCACCTGAGCTCCTGCGAATGGCTTCCCCACCTGCCCGTGGCTCCCAAGCTGGGGATGTCTACAGTTTTGGTATCATCCTT
CAGGAAATTGCCCTAAGAAGTGGGGTCTTCTATGTGGAAGGTTTGACCTCCAGCCCAAAAGAGACTCATTGAGCGTGTGACTCGGGGT
GAGCAGCCCCCATTCCGACCTTCCATGGATCTGCAGAGCCACCTGGAGGAACTGGGGCAGCTGATGCAGAGGTGCTGGGCAGAGGAT
CCTCAGGAGCGGCCACCCTTTCAACAGATCCGCCTGGCGCTGCCAAGTTCAACAAGGAGAACAGCAGCAACATCCTGGACAACCTG
CTGTCACGCATGGAACAGTACGCCAACAACCTGGAGGAACTGGTAGAGGAGAGAACACAGCCTTATCGGAGGAGAAGCGCAAAGCT
GAGGCCCTGCTTTACCAGATTCTGCCTCACTCTGTGGCTGAGCAGCTGAAGAGAGGCGAGACAGTCCAGGCTGAGGCATTTGATAGT
GTTACTATCTATTTCAGTGATATCGTGGGCTTTACAGCTCTTTCAGCAGAGAGCACACCCATGCAGGTGGTCACCCTGCTCAATGAT
CTGTACACCTGTTTTGATGCTGTCATAGACAACTTTGATGTGTACAAGGTAGAGACCATTGGTGATGCTTACATGGTGGTATCAGGG
CTCCCAGTGAGGAATGGACAGCTCCATGCCCGAGAGGTAGCCCGAATGGCACTTGCACTGCTCGATGCTGTACGCTCCTTCCGCATC
GGGCCATAGGCCCCAGGAACAGCTGCGCTTGCGCATTGGAATTCACACGGGTCCTGTGTGTGCTGGTGTGGTAGGGCTAAAGATGCCC
CGATACTGCCTCTTTGGAGACACAGTCAACACAGCTTCAAGAATGGAGTCTAATGGGGAAGCCCTCAGGATCCACTTGTCTTCGGAG
ACCAAGGCTGTGCTGGAAGAGTTCGATGGTTTCGAGCTGGAGCTCCGAGGGGATGTGGAAATGAAGGGCAAAGGCAAGGTTCGTTCC
TATTGGCTCCTCGGGGACCGGGGATGCAGCTCTCGAGCC
```

Mouse ANF-RGC protein (SEQ ID NO.: 5)

```
Met Pro Arg Ser Arg Arg Val Arg Pro Arg Leu Arg Ala Leu Leu Leu Leu Pro Pro Leu Leu Leu
Leu Arg Ser Gly His Ala Ser Asp Leu Thr Val Ala Val Val Leu Pro Val Thr Asn Thr Ser Tyr
Pro Trp Ser Trp Ala Arg Val Gly Pro Ala Val Glu Leu Ala Leu Gly Arg Val Lys Ala Arg Pro
Asp Leu Leu Pro Gly Trp Thr Val Arg Met Val Leu Gly Ser Ser Glu Asn Ala Ala Gly Val Cys
Ser Asp Thr Ala Ala Pro Leu Ala Ala Val Asp Leu Lys Trp Glu His Ser Pro Ala Val Phe Leu
Gly Pro Gly Cys Val Tyr Ser Ala Ala Pro Val Asp Arg Phe Thr Ala His Trp Arg Leu Pro Leu
Leu Thr Ala Gly Ala Pro Ala Leu Gly Ile Gly Val Lys Ala Gly Tyr Ala Leu Thr Thr Arg Thr
Gly Pro Ser His Val Lys Leu Gly Asp Phe Val Thr Ala Leu His Arg Arg Leu Gly Trp Glu His
Gln Ala Leu Val Leu Tyr Ala Asp Arg Leu Gly Asp Asp Arg Pro Cys Phe Phe Ile Val Glu Gly
Leu Tyr Met Arg Val Arg Glu Arg Leu Asn Ile Thr Val Asn His Gln Glu Phe Val Glu Gly Asp
Pro Asp His Tyr Thr Lys Leu Leu Arg Thr Val Gln Arg Lys Gly Arg Val Ile Tyr Ile Cys Ser
Ser Pro Asp Ala Phe Arg Asn Leu Met Leu Leu Ala Leu Asp Ala Gly Leu Thr Gly Glu Asp Tyr
Val Phe His Leu Asp Val Phe Gly Gln Ser Leu Gln Gly Ala Gln Gly Pro Val Pro Glu Lys
Pro Trp Glu Arg Asp Asp Gly Gln Asp Arg Arg Ala Arg Gln Arg Phe Gln Ala Ala Lys Ile Ile
Thr Tyr Lys Glu Pro Asp Asn Pro Glu Tyr Leu Glu Phe Leu Lys Gln Leu Lys Leu Leu Ala Asp
Lys Lys Phe Asn Phe Thr Met Glu Asp Gly Leu Lys Asn Ile Ile Pro Ala Ser Phe His Asp Gly
Leu Leu Leu Tyr Val Gin Ala Val Thr Glu Thr Leu Ala Gln Gly Glu Thr Val Thr Asp Gly Glu
Asn Ile Thr Gln Arg Met Trp Asn Arg Ser Phe Gln Glu Val Thr Gly Tyr Leu Lys Ile Asp Arg
Asn Gly Asp Arg Asp Thr Asp Ser Pro Leu Trp Asp Pro Met Asp Pro Glu Thr Gly Ala Phe Arg Val
Val Leu Asn Phe Asn Gly Thr Ser Gln Glu Leu Met Ala Val Ser Glu His Arg Leu Tyr Trp Pro
Leu Gly Tyr Pro Pro Asp Ile Pro Lys Cys Giy Phe Asp Asn Glu Asp Pro Ala Cys Asn Gln
Asp His Phe Ser Thr Leu Glu Val Leu Ala Leu Val Gly Ser Leu Ser Leu Val Ser Phe Leu Ile
Val Ser Phe Phe Ile Tyr Arg Lys Met Gln Leu Glu Lys Glu Leu Val Ser Glu Leu Trp Arg Val
Arg Trp Glu Asp Leu Gln Pro Ser Ser Leu Glu Arg His Ler Arg Ser Ala Gly Ser Arg Leu Thr
Leu Ser Gly Arg Gly Ser Asn Tyr Gly Ser Leu Leu Thr Thr Glu Gly Gln Phe Gln Val Phe Ala
Lys Thr Ala Tyr Tyr Lys Gly Asn Leu Val Ala Val Lys Arg Val Asn Arg Lys Arg Ile Glu Leu
Thr Arg Lys Val Leu Phe Glu Leu Lys His Met Arg Asp Val Gln Asn Glu Gln Leu Thr Arg Phe
Val Gly Ala Cys Thr Asp Pro Pro Asn Ile Cys Ile Leu Thr Glu Tyr Cys Pro Arg Gly Ser Leu
Gln Asp Ile Leu Glu Asn Glu Ser Ile Thr Leu Asp Trp Met Phe Arg Tyr Ser Leu Thr Asn Asp
Ile Val Lys Gly Met Leu Phe Leu His Asn Gly Ala Ile Cys Ser His Gly Asn Leu Lys Ser Ser
Asn Cys Val Val Asp Gly Arg Phe Val Leu Lys Ile Thr Asp Tyr Gly Leu Glu Ser Phe Arg Asp
Pro Glu Pro Glu Lys Glu Ile Glu Arg Val Thr Arg Gly Val Arg Pro Pro Phe Lys Phe Asn
Lys Glu Asn Ser Ser Asn Ile Leu Asp Asn Leu Leu Ser Arg Met Glu Asn Leu Arg Leu Glu Ala
Leu Leu Tyr Gln Ile Leu Pro His Ser Val Ala Glu Gln Leu Lys Arg Gly Glu Thr Val Gln Ala
Glu Ala Phe Asp Ser Val Thr Ile Tyr Phe Ser Asp Ile Val Gly Phe Thr Ala Leu Ser Ala Glu
Ser Thr Pro Met Gln Val Val Thr Leu Leu Asn Asp Leu Tyr Thr Cys Phe Asp Ala Val Ile Asp
Asn Phe Asp Val Tyr Lys Val Glu Thr Ile Gly Asp Ala Tyr Met Val Val Ser Gly Leu Pro Val
Arg Asn Gly Gln Leu His Ala Arg Glu Val Ala Arg Met Ala Leu Ala Leu Leu Asp Ala Val Arg
Ser Phe Arg Ile Gly His Arg Pro Gln Glu Gln Leu Arg Leu Arg Ile Gly Ile His Thr Gly Pro
Val Cys Ala Gly Val Val Gly Leu Lys Met Pro Arg Tyr Cys Leu Phe Gly Asp Thr Val Asn Thr
Ala Ser Arg Met Glu Ser Asn Gly Glu Ala Leu Arg Ile His Lle Ser Ser Glu Thr Lys Ala Val
Leu Glu Glu Phe Asp Gly Phe Asp Leu Glu Leu Arg Gly Asp Val Glu Met Lys Gly Lys Gly Lys
Val Arg Ser Tyr Trp Leu Leu Gly Asp Arg Gly Cys Ser Ser Arg Ala
```

Human ANF-RGC cDNA (SEQ ID NO.: 18)

```
ATGCCGGGGCCCCGGCGCCCCGCTGGCTCCCGCCTGCGCCTGCTCCTGCTCCTGCTGCCGCCGCTGCTGCTGCTGCTCCGGGGC
AGCCACGCGGGCAACCTGACGGTAGCCGTGGTACTGCCGCTGGCCAATACCTCGTACCCCTGGTCGTGGGCGCGCGTGGGACCCGCC
GTGGAGCTGGCCCTGGGCCCAGGTGAAGGCGCGCCCCGACTTGCTGCCGGGCTGGACGGTCCGCACGGTGCTGGGCAGCAGCGAAAAC
```

-continued
GCGCTGGGCGTCTGCTCCGACACCGCAGCGCCCCTGGCCGCGGTGGACCTCAAGTGGGAGCACAACCCCGCTGTGTTCCTGGGCCCC
GGCTGCGTGTACGCCGCCGCCCCAGTGGGGCGCTTCACCGCGCACTGGCGGGTCCCGCTGCTGACCGCCGGCGCCCCGGCGCTGGGC
TTCGGTGTCAAGGACGAGTATGCGCTGACCACCCGCGCGGGGCCCAGCTACGCCAAGCTGGGGGACTTCGTGGCGGCGCTGCACCGA
CGGCTGGGCTGGGAGCGCCAAGCGCTCATGCTCTACGCCTACCGGCCGGGTGACGAAGAGCACTGCTTCTTCCTCGTGGAGGGGCTG
TTCATGCGGGTCCGCGACCGCCTCAATATTACGGTGGACCACCTGGAGTTCGCCGAGGACGCCTCAGCCACTACACCAGGCTGCTG
CGGACCATGCCGCGCAAAGGCCGAGTTATCTACATCTGCAGCTCCCCTGATGCCTTCAGAACCCTCATGCTCCTGGCCCTGGAAGCT
GGCTTGTGTGGGGAGGACTACGTTTTCTTCCACCTGGATATCTTTGGGCAAAGCCTGCAAGGTGGACAGGGCCCTGCTCCCCGCAGG
CCCTGGGAGAGAGGGGATGGGCAGGATGTCAGTGCCCGCCAGGCCTTTCAGGCTGCCAAAATCATTACATATAAAGACCCAGATAAT
CCCGAGTACTTGGAATTCCTGAAGCAGTTAAAACACCTGGCCTATGAGCAGTTCAACTTCACCATGGAGGATGGCCTGGTGAACACC
ATCCCAGCATCCTTCCACGACGGGCTCCTGCTCTATATCCAGGCAGTGACGGAGACTCTGGCACATGGGGGAACTGTTACTGATGGG
GAGAACATCACTCAGCGGATGTGGAACCGAAGCTTTCAAGGTGTGACAGGATACCTGAAAATTGATAGCAGTGGCGATCGGGAAACA
GACTTCTCCCTCTGGGATATGGATCCCGAGAATGGTGCCTTCAGGGTTGTACTGAACTACAATGGGACTTCCCAAGAGCTGGTGGCT
GTGTCGGGGCGCAAACTGAACTGGCCCCTGGGGTACCCTCCTCCTGACATCCCCAAATGTGGCTTTGACAACGAAGACCCAGCATGC
AACCAAGATCACCTTTCCACCCTGGAGGTGCTGGCTTTGGTGGGCAGCCTCTCCTTGCTCGGCATTCTGATTGTCTCCTTCTTCATA
TACAGGAAGATGCAGCTGGAGAAGGAACTGGCCTCGGAGCTGTGGCGGGTGCGCTGGGAGGACGTTGAGCCCAGTAGCCTTGAGAGG
CACCTGCGGAGTGCAGGCAGCCGGCTGACCCTGAGCGGGAGAGGCTCCAATTACGGCTCCCTGCTAACCACAGAGGGCCAGTTCCAA
GTCTTTGCCAAGACAGCATATTATAAGGGCAACCTCGTGGCTGTGAAACGTGTGAACCGTAAACGCATTGAGCTGACACGAAAAGTC
CTGTTTGAACTGAAGCATATGCGGGATGTGCAGAATGAACACCTGACCAGGTTTGTGGGAGCCTGCACCGACCCCCCCAATATCTGC
ATCCTCACAGAGTACTGTCCCCGTGGGAGCCTGCAGGACATTCTGGAGAATGAGAGCATCACCCTGGACTGGATGTTCCGGTACTCA
CTCACCAATGACATCGTCAAGGGCATGCTGTTTCTACACAATGGGGCTATCTGTTCCCATGGGAACCTCAAGTCATCCAACTGCGTG
GTAGATGGGCGCTTTGTGCTCAAGATCACCGACTATGGGCTGGAGAGCTTCAGGGACCTGGACCCAGAGCAAGGACACACCGTTTAT
GCCAAAAAGCTGTGGACGGCCCCTGAGCTCCTGCGAATGGCTTCACCCCCTGTGCGGGGCTCCCAGGCTGGTGACGTATACAGCTTT
GGGATCATCCTTCAGGAGATTGCCCTGAGGAGTGGGGTCTTCCACGTGGAAGGTTTGGACCTGAGCCCCAAAGAGATCATCGAGCGG
GTGACTCGGGGTGAGCAGCCCCCCTTCCGGCCCTCCCTGGCCCTGCAGAGTCACCTGGAGGAGTTGGGGCTGCTCATGCAGCGGTGC
TGGGCTGAGGACCCACAGGAGAGGCCACCATTCCAGCAGATCCGCCTGACGTTGCGCAAATTTAACAGGGAGAACAGCAGCAACATC
CTGGACAACCTGCTGTCCCGCATGGAGCAGTACGCGAACAATCTGGAGGAACTGGTGGAGGAGCGGACCCAGGCATACCTGGAGGAG
AAGCGCAAGGCTGAGGCCCTGCTCTACCAGATCCTGCCTCACTCAGTGGCTGAGCAGCTGAAGCGTGGGGAGACGGTGCAGGCCGAA
GCCTTTGACAGTGTTACCATCTACTTCAGTGACATTGTGGGTTTCACAGCGCTGTCGGCGGAGAGCACACCCATGCAGGTGGTGACC
CTGCTCAATGACCTGTACACTTGCTTTGATGCTGTCATAGACAACTTTGATGTGTACAAGGTGGAGACAATTGGCGATGCCTACATG
GTGGTGTCAGGGCTCCCTGTGCGGAACGGGCGGCTACACGCCTGCGAGGTAGCCCGCATGGCCCTGGCACTGCTGGATGCTGTGCGC
TCCTTCCGAATCCGCCACCGGCCCCAGGAGCAGCTGCGCTTGCGCATTGGCATCCACACAGGACCTGTGTGTGCTGGAGTGGTGGGA
CTGAAGATGCCCCGTTACTGTCTCTTTGGGGATACAGTCAACACAGCCTCAAGAATGGAGTCTAATGGGGAAGCCCTGAAGATCCAC
TTGTCTTCTGAGACCAAGGCTGTCCTGGAGGAGTTTGGTGGTTTCGAGCTGGAGCTTCGAGGGGATGTAGAAATGAAGGGCAAAGGC
AAGGTTCGGACCTACTGGCTCCTTGGGGAGAGGGGGAGTAGCACCCGAGGC Human ANF-RGC protein (SEQ ID NO.: 19)
MPGPRRPAGSRLRLLLLLLLPPLLLLLRGSHAGNLTVAVVLPLANTSYPWSWARVGPAVELALAQVKARPDLLPGWTVRTVLGSSEN
ALGVCSDTAAPLAAVDLKWEHNPAVFLGPGCVYAAAPVGRFTAHWRVPLLTAGAPALGFGVKDEYALTTRAGPSYAKLGDFVAALHR
RLGWERQALMLYAYRPGDEEHCFFLVEGLFMRVRDRLNITVDHLEFAEDDLSHYTRLLRTMPRKGRVIYICSSPDAFRTLMLLALEA
GLCGEDYVFFHLDIFGQSLQGGQGPAPRRPWERGDGQDVSARQAFQAAKIITYKDPDNPEYLEFLKQLKHLAYEQFNFTMEDGLVNT
IPASFHDGLLLYIQAVTETLAHGGTVTDGENITQRMWNRSFQGVTGYLKIDSSGDRETDFSLWDMDPENGAFRVVLNYNGTSQELVA
VSGRKLNWPLGYPPPDIPKCGFDNEDPACNQDHLSTLEVLALVGSLSLLGILIVSFFIYRKMQLEKELASELWRVRWEDVEPSSLER
HLRSAGSRLTLSGRGSNYGSLLTTEGQFQVFAKTAYYKGNLVAVKRVNRKRIELTRKVLFELKHMRDVQNEHLTRFVGACTDPPNIC
ILTEYCPRGSLQDILENESITLDWMFRYSLTNDIVKGMLFLHNGAICSHGNLKSSNCVVDGRFVLKITDYGLESFRDLDPEQGHTVY
AKKLWTAPELLRMASPPVRGSQAGDVYSFGIILQEIALRSGVFHVEGLDLSPKEIIERVTRGEQPPFRPSLALQSHLEELGLLMQRC
WAEDPQERPPFQQIRLTLRKFNRENSSNILDNLLSRMEQYANNLEELVEERTQAYLEEKRKAEALLYQILPHSVAEQLKRGETVQAE
AFDSVTIYFSDIVGFTALSAESTPMQVVTLLNDLYTCFDAVIDNFDVYKVETIGDAYMVVSGLPVRNGRLHACEVARMALALLDAVR
SFRIRHRPQEQLRLRIGIHTGPVCAGVVGLKMPRYCLFGDTVNTASRMESNGEALKIHLSSETKAVLEEFGGFELELRGDVEMKGKG
KVRTYWLLGERGSSTRG As noted above, the present invention is not necessary limiting to these forms, however, and may also include the human form of the protein or any other allelic, species and induced variants thereof. Induced variants preferably show at least 90%, 95% or 99% sequence identity at the nucleic acid or amino acid sequences above.

The "deficient ANF-RGC" or a "deficiency" in ANF-RGC may refer to any mutation (including a substitution, deletion, addition, or otherwise) that would negatively alter or diminish its function, particularly in accordance with the phenotypic traits discussed herein. In certain aspects, the mutation is to at least a portion of the ATP-regulated module ("ARM") of ANF-RGC, which includes at least the amino acids spanning positions 481-771 of the ANF-RGC protein. For example, in certain embodiments, the mutation is to the ATP-ST region, which is contained within the seven amino acids spanning positions 669-675 of the ANF-RGC protein and has the amino acid sequence WTAPELL (SEQ ID NO.: 3). Mutations may also, or alternatively, be provided to other regions of ANF-RGC, particularly its ARM domain, that are functionally and/or structurally similar to ATP-ST or result in a phenotypic change similar to that of a mutation to the ATP-ST region. Such other regions may include, but are not limited to, $^{631}$SerSerAsnCysValValAspGlyArg$^{639}$ (SEQ ID NO.: 15), $^{503}$GlyArgGlySerAsnTyrGly$^{509}$ (SEQ ID NO.: 16), $^{642}$ValLysIleGlyAspPheGlyMet$^{649}$ (SEQ ID NO.: 17) of the ANF-RGC protein. For a discussion of the function of each region see Burczynska et al., *Mol. Cell. Biochem* (2007) 301:93-107, and Duda et al. *Peptides.* 2005 June; 26(6):969-84, the contents each of which are incorporated herein by reference. Mutations to certain single amino acid residues within the ARM domain also may result in diminished ANF/ATP signal transmission, i.e. reduced cyclic GMP production. Other than residues associated with the sequences above, such single site residues include, but are not limited to, lysine$^{535}$, glutamate$^{555}$, and aspartate$^{646}$. For a discussion of the function of each of these amino acids see Duda et al. *Peptides.* 2005 June; 26(6):969-84, the contents of which are incorporated herein by reference.

The foregoing mutations are not limited to the sequences provided and may also include other allelic, species and induced variants thereof. Induced variants preferably, though not exclusively, show at least 90%, 95% or 99% sequence identity at the nucleic acid or amino acid sequences above. A mutation to any of the foregoing regions or sequences may include any substitution, deletion, addition, or the like to this region that would measurably alter, particularly diminish, the catalytic activity of ANF-RGC protein, thus, its ability to produce cyclic GMP. In certain aspects of the invention the mutation includes the substantial deletion of each of the amino acids in this region. In further aspects, the mutation includes the deletion of at least the entire 7 amino acid ATP-ST sequence.

In certain aspects, a mutation to the ANF-RGC protein, particularly the ARM or ATP-ST region, results in a measurable reduction of ligand-stimulated ANF-RGC activity. As used herein, the term "ligand-stimulated ANF-RGC" or "ligand-stimulated guanylate cyclase activity" refers to a decrease of ANF-RGC activity associated with stimulation of cyclic GMP production by extracellular ligands such as, but not limited to, ANF and/or BNP. In further aspects, it refers to a measurable reduction of cyclic GMP production within the cell.

As supported in the Examples below, a decrease in such activity was observed in an array of tissues including cardiac tissue, renal tissue, and adrenal tissue. In certain aspects, the deletion of the ATP-ST region in both homozygous and heterozygous mice resulted in a reduction of ANF-RGC-mediated cyclic GMP production activity of greater than 50% in heart tissue and kidney tissue and greater than 40% in adrenal gland tissue. The lowered cyclic GMP production in kidney results in one or more of (a) lower excretion of sodium and water, (b) increased sodium reabsorption in the distal convoluted tubule and cortical collecting duct of the nephron; or (c) increased rennin secretion, thereby activating the rennin-angiotensin system. In the adrenals, it will lead to increased aldosterone secretion. To this end, such effects may be correlative with high blood pressure or hypertension.

In further aspects, mutations to the ARM or ATP-ST also result in tissue hypertrophy. Such hypertrophy is demonstrated below in cardiac and renal tissues. In certain aspects, the deletion of the ATP-ST region in both homozygous and heterozygous mice resulted in an increase in the weight of cardiac and/or renal cells or tissue of greater than 5%. Such effects are correlative with ventricular hypertrophy and also with high blood pressure. They may also be correlative with lower release of fatty acids from adipose tissue, thus leading to increased accumulation of body fat and obesity.

In further aspects of the present invention, the mutation of the ARM or ATP-ST region minimizes or results in no change to basal guanylate cyclase activity. As used herein, the term "basal guanylate cyclase activity" refers to cyclic GMP production irrespective of ANF-RGC activation. In certain aspects, it refers to a base level of cyclic GMP production by the ANF-RGC protein or other proteins within the cell without activation by the ANF, BNP, or any other extracellular ligand.

The deficiency to one or both ANF-RGC alleles (or to one or both alleles encoding the ATP-ST region) can be achieved by modification of the endogenous gene, usually, through a deletion, substitution or addition to a coding region of the gene. The modification can prevent synthesis of a gene product, but preferably results in the expression of a gene product lacking its native functional activity (e.g. cyclic GMP production). Such deficiencies may be achieved using any standard technique for producing transgenic animals with an altered genome (See, for example, Manipulating the Mouse Genome, *Current Protocols in Molecular Biology*, John Wiley, 2001, the contents of which are incorporated herein by reference).

In certain non-limiting embodiments, for example, mutations to the ANF-RGC protein are achieved by homologous recombination between an endogenous gene in a mouse embryonic stem (ES) cell and a targeting construct. Typically, the targeting construct contains a positive selection marker flanked by segments of the gene to be targeted. Usually the segments are from the same species as the gene to be targeted (e.g., mouse). However, the segments can be obtained from another species, such as human, provided they have sufficient sequence identity with the gene to be targeted to undergo homologous recombination with it. Typically, the construct also contains a negative selection marker positioned outside one or both of the segments designed to undergo homologous recombination with the endogenous gene (see U.S. Pat. No. 6,204,061). Optionally, the construct also contains a pair of site-specific recombination sites positioned within or at the ends of the segments designed to undergo homologous recombination with the endogenous gene. The construct is introduced into ES cells, usually by electroporation, and undergoes homologous recombination with the endogenous gene introducing the positive selection marker and parts of the flanking segments into the endogenous gene. ES cells having undergone the desired recombination can be selected by positive and negative selection. Positive selection selects for cells that have undergone the desired recombination, and negative selection selects against cells that have undergone negative recombination. These cells are obtained from preimplantation embryos cultured in vitro. Bradley et al., Nature 309, 255 258 (1984) (incorporated by reference in its entirety for all purposes). Transformed ES cells are combined with blastocysts from a non-human animal. The ES cells colonize the embryo and in some embryos form or contribute to the germline of the resulting chimeric animal. See Jaenisch, Science, 240, 1468 1474 (1988) (incorporated by reference in its entirety for all purposes). Chimeric animals can be bred with nontransgenic animals to generate heterozygous transgenic animals. Heterozygous animals can be bred with each other to generate homozygous animals. Either heterozygous or homozygous animals can be bred with a transgenic animal expressing the recombinant gene. Expression of the recombinase results in excision of the portion of DNA between introduced restriction sites, if present.

Functional inactivation can also be achieved for other species, such as rats, rabbits and other rodents, bovines such as sheep, caprines such as goats, porcines such as pigs, and bovines such as cattle and buffalo, are suitable. For animals other than mice, nuclear transfer technology is preferred for generating functionally inactivated genes. See Lai et al., Sciences 295, 1089 92 (2002). Various types of cells can be employed as donors for nuclei to be transferred into oocytes, including ES cells and fetal fibrocytes. Donor nuclei are obtained from cells cultured in vitro into which a construct has been introduced and undergone homologous recombination with an endogenous gene, as described above (see WO 98/37183 and WO 98/39416, each incorporated by reference in their entirety for all purposes). Donor nuclei are introduced into oocytes by means of fusion, induced electrically or chemically (see any one of WO 97/07669, WO 98/30683 and WO 98/39416), or by microinjection (see WO 99/37143, incorporated by reference in its entirety for all purposes). Transplanted oocytes are subsequently cultured to develop into embryos which are subsequently implanted in the oviducts of pseudopregnant female animals, resulting in birth of transgenic offspring (see any one of WO 97/07669, WO 98/30683 and WO 98/39416). Transgenic animals bearing heterozygous transgenes can be bred with each other to generate transgenic animals bearing homozygous transgenes.

In certain aspects, the transgenic animals of the present invention may be used to study the effects of ANF-RGC mediated cyclic GMP production. By way of non-limiting example, such transgenic animals may be used to study the effects that ligand-stimulated ANF-RGC cyclic GMP production has on cardiac and/or renal homeostasis. Such animals may be similarly used to study the effects of ANF-RGC on tissues such as cardiac tissue, renal tissue, and adrenal tissue. In further, or alternative, aspects, it may be used to study the phenotypic traits exhibited with diminished ANF-RGC activity and/or reduced cyclic GMP production, such as, but not limited to, hypertension, tissue hypertrophy, or the like.

The transgenic animals of the present invention, or cells derived therefrom, also may be used for various methods of screening compounds. In one aspect, the transgenic animals of the present invention may be used to screen or identify compounds, small molecules, proteins/peptides, or other therapeutics that reduce or otherwise decrease hypertension, other than through modulation of ANF-RGC activity. By way of example, the mutations to ANF-RGC, particularly its ARM or ATP-ST region, causes a dramatic decrease in cyclic GMP production, which results in increased blood pressure. Accordingly, therapeutic agents for the treatment or prevention of hypertension may be screened in studies using the transgenic animals of the present invention. The transgenic animals of the present invention may be treated with a test therapeutic that modulates cardiac homeostasis, so as to reduce blood pressure. Such an agent may target a pathway overlapping with or, in certain embodiments, separate from the ANF-RGC mediated pathway.

The transgenic animals of the present invention may also be used in models to study ANF-RGC over-expression and to screen for therapeutics to control such expression. To this end, native ANF-RGC may be re-introduced into a targeted tissue of a transgenic animal of the present invention by standard means, such as, but not limited to, transfection with a viral or non-viral vector. Expression of ANF-RGC may be controlled by the upstream region of the vector to the ANF-RGC gene, which may include promoters, enhancers, or other elements adapted to provide high or constitutive expression levels within the cell. Such promoters, enhancers, and other elements are well-described in the art and will be readily apparent to one of skill in the art. In certain aspects, the promoter region may be adapted to control expression only in the targeted tissue/cell type. By way of non-limiting example, expression in the desired cell type may be controlled using a promoter region of a high or constitutively expressed protein within that cell. Examples of such promoters include, but are not limited to, the myosin heavy chain promoter in cardiac tissue, the ksp-cadherin promoter in renal tissue, and disabled-2 promoters in adrenal glomerulosa tissue. The phenotypic traits associated with over-expression can be studied and compared against the ANF-RGC deficient animal as a control. Such models may also be used to screen for compounds, small molecules, proteins or other therapeutics that modulate ANF-RGC activity by comparing its effect on cyclic GMP production and/or hypertension in the animal that is ANF-RGC deficient versus the transgenic animal where functional ANF-RGC has been reintroduced into one or more tissues using the foregoing method.

In even further embodiments, the transgenic animals of the present invention may be used to determine a toxicity profile of compounds that are known to modulate ANF-RGC, including the mutated or deleted portions thereof. The toxicity profile can be determined, for example, by monitoring expression of a large number of mRNAs or proteins encoded by the cells of the animal. Arrays for expression monitoring and equipment and procedures for using them are available from Affymetrix. The expression profile of an inhibitor under test can be compared with profiles of other compounds that are known to have or not have undesired side effects (see U.S. Pat. Nos. 5,811,231; 6,040,138). Similarity of profile with one or more compounds not prone to side effects signals that an inhibitor is not likely to have side effects itself, and thus remains a candidate for further screening (e.g., in clinical trials). Similarity of profile with one or more compounds having side effects signals that an inhibitor may itself be prone to side effects. Because these side effects do not arise as a result of the inhibitor's interaction with ANF-RGC, it may be possible to redesign an inhibitor such that it retains its ANF-RGC modulation characteristics but loses the undesired side effects. The transgenic animals of the present invention are similarly useful to distinguish potential mechanisms of action and evaluate structure activity relationships of pharmacological agents with potential activity in treating hypertension.

The transgenic animals of the invention may also be used as control for purposes of comparison with transgenic animal models of hypertension that have functional ANF-RGC. To this end, they may be used to establish a baseline level of ANF-RGC activity (or non-activity) and to act as a control species during test trials with the therapeutic or drug targeting wildtype ANF-RGC in a normal mouse or animal.

The following are examples supporting the foregoing invention. They are not to be construed as limiting to the invention.

EXAMPLES

Example 1

Generating Transgenic Mouse Lacking the ATP-ST Region of ANF-RGC

Two fragments (5' arm and 3' arm) of the mouse ANF-RGC gene were amplified from the mouse genomic DNA by PCR. They comprised the following genomic sequences: 5'-arm: from intron 8 to intron 13; 1800 bp (part of intron 8, exon 9, intron 9, exon 10, intron 10, exon 11, intron 11, exon 12, intron 12, exon 13, part of intron 13); 3'-arm: from intron 13 to intron 18; 2570 bp (part of intron 13, exon 14, intron 14, exon 15, intron 15, exon 16, intron 16, exon 17, intron 17, exon 18, part of intron 18).

5'-arm: Sequence (SEQ ID NO.: 6)
```
GGCTGATGAGTTAGCGGAAGCTTCTAGATGAGGTGACTCACCCGGAC
CCAGGACTTGGGTGGTTAAGATAGGAAGATCTTGCTGTAAGTCTGAG
GCTAGCCCATCCGTCTCTCATAAAACCAGAGCCAAACAAAAGAACAG
GCTAACCCCCAGCTCTGCCTTCACTTGCTCACTCTGACATTGTCTTA
AGTGAGGGTTGCAGTTACAGCCTCTGTAACAAGGCCCTCTCAAAGGT
CAAATGACATAGTCTAAGTAAGCACGCAGGTATGAGTCTAATACACT
ACACAAAGGCGGGTGGGAGCTGGCATGGGTAGCTTACACCTGCAATC
ATTACTACAAGTTCAGGCAACCCTGAGCTAAAGAGTGAGAGCCTCTC
TCTGCAAGGTAACAGATAAAGGGGCAGTTGTGATTGAATCTAGAACT
TCCAGGATGCAGAAATGACCTCTGGGCTGACCAATAGATGACTATTG
TTCATCTCTGTAGCGAGCGTCCAATTATGGCTCCCTGCTAACCACGG
AGGGCCAGTTCCAAGTCTTTGCCAAGACAGCATACTATAAGGTAGGT
CTGGGGCAAGATTGTAGAGTGTGCTCTGAGGACTAAGAGATGGTTCT
GAGTGGGCTGCCAGGGACAGGGGTGGTCCCAGGGCAGGGTGGGCTTT
TAGAAGCAGGTAGAGAGCTGGGGTCATGGATGGGTTTCAGAAGCAGA
TGGGAGTCTCAGGTCATCTCCTGAATAATAAGTTTCCATTTCTTGCT
CAGGGCAACCTCGTGGCTGTGAAACGTGTGAACCGGAAACGCATTGA
GTTGACACGAAAAGTCCTGTTTGAACTTAAACATGTTAATTTACGGG
GGAACAAGGCTGTGGCTTGGGAAAGGGCCCCATGGGTACTCCCAAGA
GAGTCGGCCAACAGAACTTGATTATGGAAGGATCTATACATCTGGGA
TGGGCCCTTGAGTCTTGTGGGTAGGAAAAAGGAGATCAGTCATGAGA
GATCACTGGGTCCTCCAGGGTCCAGACGGGTTGTCCTCATAGGTACA
GCCAGGAAATCAAGGGGTTAGGGAGCAGATGCTGAGAAAGAATGTTA
ATCAACACATGACTTGGTGAGGTATGAAGCCTCTGCCAGGCCTTGAT
GCTGCCCCCACTTGCAGATGCGGGATGTGCAGAATGAGCACTTGACC
```

-continued

AGATTTGTGGGAGCTTGTACCGACCCTCCCAACATCTGTATCCTCAC
AGAGTACTGTCCCCGTGGGAGCCTACAGGTGAGCGGGACAAGAGGGA
GTGTGTCGAGAAGCCCGGGGTTCCAGCCCTGGCTCTTACCCCATTGA
TCACATGAGCCCAGATAAGCTTCCTCTTTCTGGCCATTCTTGGCCTC
TCTGTAAATGGGGGTTGGGGGCGGGCATGGCACTACAGCAAATCCAA
AGTGTCCAAGCTTACGCCAGTAGCTCCCTTGCTACCCTCCTCCTGAC
TCCCAAGGGGGGTCTGACTCCTTGCTTGCCCCAGCAGGACATTCTAG
AGAATGAGAGTATTACCCTGGACTGGATGTTTCGGTACTCACTCACC
AATGACATTGTCAAGGTGAGTCCCAGAGGAGCTCAACTGGATGCCAG
GCAAGGGCTGGGCATGGTTGGAAGTCACGAACCCGAGCCCTCTCGCC
TTCCTAAATATTCCAGGGAATGCTCTTTCTACACAACGGGGCCATTG
GTTCCCATGGGAACCTCAAGTCATCCAACTGCGTGGTAGATGGACGT
TTTGTGTTAAAGATCACAGACTATGGGCTCGAGAGCTTCAGAGACCC
GGAGCCAGAGCAAGGACACACCCTCTTTGCCAGTAAGTCTGACTCTT
GACCCTAGGCCTCTGCTGCCAACACAAGCTCAGAAGGGAAACTGAGG
CCTAACCTCTGCATGACTTGGGTATACCTCTCATCTGCAAGGCTCAA
TCTTCATTGGTTTAAAAAGGAGGTCAGACCAAGTGGTCACTGGGTTC
TCAGCACTGTGCCGTGTGCCACAGGAGTCCCTAGCTACACCCTTGAT
CCCTGATTATCTTAAACCATATGACAAGCTTATTTTTCGCAGCC

3'-arm: Sequence (SEQ ID NO.: 7)
TTCTCAGAATTATCACACCATCCTGTCTTACTTTTTTTTTCATTTAA
ATATTTATTTATTTATTTCCTGCATAGTTGAATACATCATTGCTCTG
CTTCAGACACAGCAAGAAGGAGGGCATCAGAATCTCATTACCCAGAT
GATCGTGAGCCACCATGTGGTTGCTGGGAATTGAACTCAGGACCTCT
AGAAGAGCAGTCAGTGTTCTTAACCACTGAGCTATTTTTCCAGGCCC
CCACCCCTGTCTTACTTTTATTATAGCATTTATTACCCATGAAATAT
AATATTCATTTGCTAGTTTTTCTTTTTCCCATCATAATGTAAAGTCC
CTTATCCCTTCTATGACTCCCAACCTCTGATCCACAGAAAAACTGTG
GACTGCACCTGAGCTCCTGCGAATGGCTTCCCCACCTGCCCGTGGCT
CCCAAGCTGGGGATGTCTACAGTTTTGGTATCATCCTTCAGGAAATT
GCCCTAAGAAGTGGGGTCTCCTATGTGGAAGGTTTGGACCTCAGCCC
AAAAGGTGAGGATCACTTGGCCTATACCCCAGCCAATCTTGATGAAT
CTACCACCAGAGAGGGAACCTCTCCAAACACCCCTACCATTCCTTCT
GGAGTGGGGAGTCAGCCACTATCCTTTGCTCTGTGGCTGCTAGTGAC
CAGTCCACTCTGTGCTCTGGTCTGGACTTGTCCCACCTAGACAGGTC
TATCCCAGCTGGTTGCCCAGCTAGGCTTGCCGCTCTTCAGTGCGTGC
CCCTTCCACACAGAGATCATTGAGCGTGTGACTCGGGGCGAGCAGCC
CCCATTCCGACCTTCCATGGATCTGCAGAGCCACCTGGAGGAACTGG
GGCAGCTGATGCAGAGGTGCTGGGCAGAGGATCCTCAGGAGCGGCCA
CCCTTTCAACAGATCCGCCTGGCGCTGCGCAAGTTCAACAAGTTAGT
GGTCTCTCCCACTACAACCACTGTAAATCCCACACTTAAATCTTCTT
CTACAGTGGCAGCCCACAGAAGCCACCACAGCCTCAAAGGCATCTGC
ATAGCTGGATGACTTGGCTGTCCCAACAGCTCCTTACCATTCACTAC
TCCTTCCTCTGCCAACATTGATACCCCACACCCTTTCCTGCCCACGG
CCCTGTACTAACCCCCAGACTTCCATCTCTTTTTTCCAGTATGCCCA
CCGGCTAGTTCTCCCACTCATGTCTCTCTGCTGCCTGTCACTATCCT
CAGCTCACCCTGCTTCTCTCCCTCCCCACCTCCTTCAAACTCACTTG
TGTTCAATAAGAATAAGTAAGAACTCCAGCTGGTCAGAGAAGCAGGT
AGATGTCTGTGGGTTCAAGGCCAGTTGTTCTTTTCACCTAAAACCCC
TGATAATGTGAATAGATCCAGCTATGGCTACCTAGAGAGACCCTGTC
TTTAAGGGTGGGGCAGGCATGGTGAGTGCCTGAATAATGTGGGCACT
GCCAGGAAGAACCAGTCATCCCATCTCATCTCATCTGCTCCCCCCGC
CCCCCGCCCCTGTAACCCATGGCCCTCAGGGAGAACAGCAGCAACAC
CCTGGACAACCTGCTGTCACGCATGGAACAGTACGCCAACAACCTGG
AGGAACTGGTAGAGGAGAGAACACAGGCTTATCTGGAGGAGAAGCGC
AAAGCTGAGGCCCTGCTTTACCAGATTCTGCCTCAGTGAGTTCTAAA
CTCTGCACGCGCGCGCGCGCGCGCGCACACACACACACACA
CACACACACACACACACACAAACGTATAGCCCTGTCCCCATCCCA
TCTCACCTCTTGGTCTCTACCTGCCCTCTCCCCTCAGCTCTGTGGCT
GAGCAGCTGAAGAGAGGCGAGACAGTCCAGGCTGAGGCATTTGATAG
TGTTACTATCTATTTCAGTGATATCGTGGGCTTTACAGCTCTTTCAG
CAGAGAGCACACCCATGCAGGTAAGCCGGGTTCAGCCACAGCAACA
GGCCAGGTAGGTCAGCTTGCCACCTGGTTAGTACTCTCCACTTGTCC
CTGGTGGGAGCCCTCATTCACCATTTCTCTTGGCTTCCTTTGCCTTC
CAGGTGGTCACCCTGCTCAATGATCTGTACACCTGTTTTGATGCTGT
CATAGACAACTTTGATGTGTACAAGGTGAGGTTATGAGTAGAGACAA
GAAAGACAGGCAGACATGGACAGTCAGAAAATGTTCAGAGGGATCCT
CTGAAACAAACAAAACAAAACAAAAAAGGCCAGGCATGGTGGTGCAC
ACCTTTAATCCTACCACTTGAAGATAGATGCAGGGAAATCTATGAGT
TTGAGGCCAGCCTGAGCAAGTTTCAGGACAGGACCCCATAGCTACAC
TCAAAGAAACTCTGTCTTGAAAAAACAAAGGAGAAGAAGGAAGAGGA
GGAGGAGGAGAAAGGGGAGGAAGAAGAGGAGGAGGAGAAGGAGGAGA
AGGAAGAAGAAGAAGGAGAAGGAAGA They were amplified from ES cells genomic DNA using the following primers:

```
5'-arm Forward primer
                                  (SEQ ID NO.: 8)
5'-GGCTGATGAGTTAGCGGAAGCTTCTAGATG-3'

5'-arm Reverse primer
                                  (SEQ ID NO.: 9)
5'-GGCTGCGAAAAATAAGCTTGTCATATGGTT-3'

3'-arm Forward primer
                                  (SEQ ID NO.: 10)
5'-TTCTCAGAATTATCACACCATCCTGTCTTA-3'

3'-arm Reverse primer
                                  (SEQ ID NO.: 11)
5'-TCTTCCTTCTCCTTCTTCTTCTTCCTTCTC-3'
```

These two fragments were subcloned into HSV-TK (herpes simplex virus thymidine kinase) vector. The vector contains two multiple cloning sites (MCS) separated by PGK neo cassette (a selectable gene marker, the neomycin resistance gene, for selection) flanked by two LoxP sequences (LoxP sequence: ATAACTTCGTATAATGTTATGCTATAC-GAAGTTAT (SEQ ID NO: 12)). The 5' arm was subcloned into MCS2 and 3' arm into MCS1.

The $^{669}$WTAPELL$^{675}$ motif is located within the exon 14 of the ANF-RGC gene. The motif was removed by site-directed mutagenesis. The Δ$^{669}$WTAPELL$^{675}$ mutant of the targeting vector was identified by sequencing. The 5'-arm-loxP-PGKneo-loxP-3'-arm fragment was released form the vector by enzymatic digestion. The reaction mixture was resolved on agarose gel, the appropriate band was excised from the gel and the DNA was extracted and purified.

The purified DNA was electroporated into mouse ES cells. More specifically, twenty five µg of purified DNA was mixed with the mouse 129 embryonic stem cells (ES cells) and the electroporation was carried out at 230V, 500 µF. The electroporated cells were plated and fed with culture Dulbecco's modified Eagle's medium. 24 hr after the electroporation antibiotic G418 (neomycin) was added to the media and the cells were cultured for 12 days. Only the neomycin resistant colonies survived at the 12 days of selection. They were picked up and individually seeded and grown in the presence of G418. The resistance to neomycin indicated that a recombination with the targeting vector has occurred.

The genomic DNA was isolated from the cells and used as template for long range PCR. The sequences of primers for PCR amplification were located outside the 5'- and 3'-arms.

```
Forward primer:
                                  (SEQ ID NO.: 13)
5'-AGAGGCACCTTCGGAGCGCTGGCAGTCGGC-3'

Reverse primer:
                                  (SEQ ID NO.: 14)
5'-CTGGGAGCCCTGATACCACCATGTAAGCAT-3'
```

The amplified fragments were resolved on agarose gel, eluted from the gel, and sequenced to identify the clones with homologous recombination. The identified positive clones (with homologous recombination) were used for injection into blastocytes.

The ES cells with homologous recombination were injected into blastocytes and implanted into pseudo-pregnant mice. The resulting pups are considered chimeric in their genetic makeup as they consist of tissues deriving from both the microinjected ES cell and the endogenous host blastocyst genome. The offspring was genotyped. 8 chimeras were identified (3 females and 5 males).

The chimera mice were bred with wildtype CD 1 mice to determine the germline transmission. The offspring with dark eyes-indicative of the germline transmission, was genotyped to identify the heterozygotes. The male heterozygotes identified were bred with Hprt-Cre mice to remove the PGKneo cassette from intron 13 (When male mice carrying a neomycin selection cassette flanked by loxP sites are mated to female mice heterozygous for Cre-deleter inserted into Hprt gene, the neo cassette is excised without detectable mosaicism). The offspring was genotyped for removal of the LoxP-PGKneo cassette and of the $^{669}$WTAPELL$^{675}$ motif. One LoxP site was retained to facilitate the genotyping.

4 positive heterozygotes were identified, 1 male and 3 females. The heterozygotes were mated. Genotyping of the pups showed that 2 homozygotes for the $^{669}$WTAPELL$^{675}$ motif deletion [($^{669}$WTAPELL$^{675}$)$^{-/-}$] were obtained, 6 were heterozygotes [($^{669}$WTAPELL$^{675}$)$^{+/-}$] and 4 wildtype. FIG. 1 provides a agarose gel demonstrating ANF-RGC DNA bands for the wildtype and knock-out mice. Lane 1 is a molecular weight marker. Lanes 2 and 3 illustrate a heterozygous and homozygous, respectively, knock-out of the ANF-RGC gene. Lane 4 illustrates the wild type mouse.

Example 2

$^{669}$WTAPELL$^{675}$ Null Mice ANF Loses the Control Over Adrenal, Renal and Cardiac Activities Heart, kidneys and adrenals were removed from 6 weeks old wt, ($^{669}$WTAPELL$^{675}$)$^{+/-}$ and ($^{669}$WTAPELL$^{675}$)$^{-/-}$ female mice. The particulate fraction of each organ was prepared and analyzed for basal (B) and ANF/ATP-stimulated (S) guanylate cyclase activity. Mean±SD of three assays for each organ is shown in FIG. 2.

The animals from Example 1 were sacrificed and the tissues, heart, kidneys, and adrenal glands were removed from each animal. The tissues were quickly frozen in liquid nitrogen, powdered by mortal and pestle, and homogenized in 50 mM Tris-HCl/10 mM MgCl$_2$ buffer pH 7.4, aliquoted and stored at −80° C. until used. On the day of the experiment an aliquot of the particulate fraction suspension of each tissue (heart, kidney, and adrenal gland) from every animal [wild type, (WTAPELL)$^{+/-}$, (WTAPELL)$^{-/-}$] was thawed and 2.5 µl of the suspension was assayed for guanylate cyclase activity in an assay mixture consisting of 10 mM theophylline, 15 mM phosphocreatine, 20 µg creatine kinase and 50 mM Tris-HCl, pH 7.5 in the absence or presence of 10-7 M ANF and 0.5 mM ATP. The total assay volume was 25 µl. The reaction was initiated by addition of the substrate solution (4 mM MgCl$_2$ and 1 mM GTP, final concentration) and maintained by incubation at 37° C. for 10 min. The reaction was terminated by the addition of 225 µl of 50 mM sodium acetate buffer, pH 6.2 followed by heating on a boiling water bath for 3 min. The amount of cyclic GMP formed was determined by radioimmunoassay.

Figure 2:
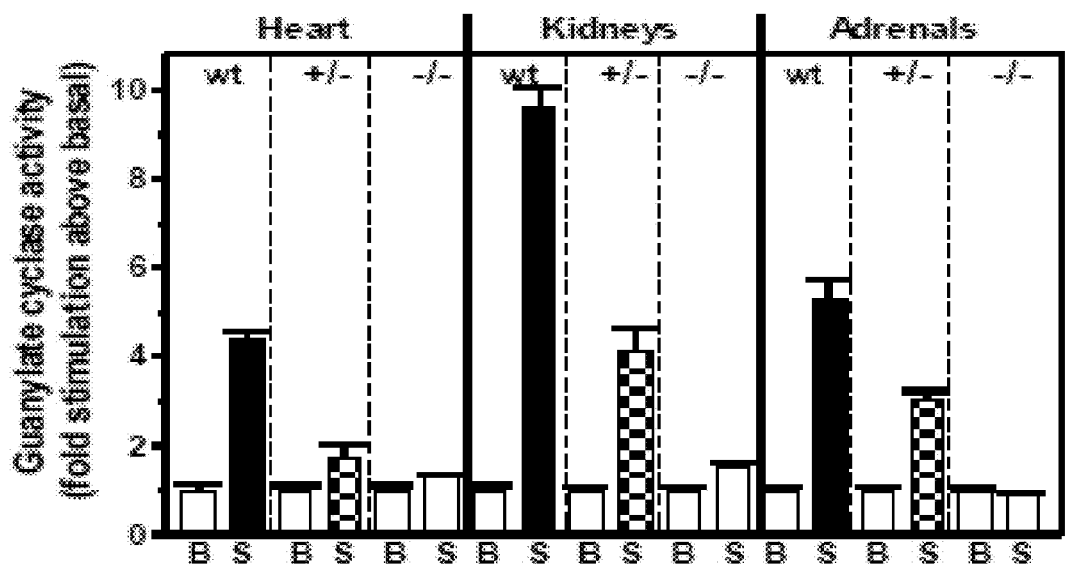
FIG. 2 illustrates basal (B) and ANF/ATP-stimulated (S) guanylate cyclase activity in heart, kidney, and adrenal gland tissue of wildtype, ($^{669}$WTAPELL$^{675}$)+/− and ($^{669}$WTAPELL$^{675}$)−/− female mice.

As shown in FIG. 2, in the normal mice ANF/ATP stimulates guanylate cyclase activity in the heart, kidney and adrenal gland. ANF-RGC stimulation is totally lost in the ($^{669}$WTAPELL$^{675}$)−/− mice and partially in the heterozygous (+/−) mice. The basal cyclase activity in membranes of these organs is unaffected, however, as these levels are comparable for wildtype (wt) mice, ($^{669}$WTAPELL$^{675}$)+/− and ($^{669}$WTAPELL$^{675}$)−/− animals being 25±5, 40±7 and 70±9 pmol cGMP min−1 (mg prot)−1 for heart, kidney and adrenal, respectively. These results validate and for the first time demonstrate in vivo the physiological significance of the $^{669}$WTAPELL$^{675}$ motif for the control of ANF-RGC signal transduction in the heart kidney and adrenal gland.

Example 3

Absence of the $^{669}$WTAPELL$^{675}$ Motif in ANF-RGC Gene Causes Cardiac and Renal Hypertrophy The animals from Example 1 were sacrificed and the total body weight of each animal was determined. The tissues, heart and kidney, were removed from each animal and their weight was determined. The ratio of the tissue (heart or kidney) weight (in mg) to body weight (in g) was calculated.

Figure 3:
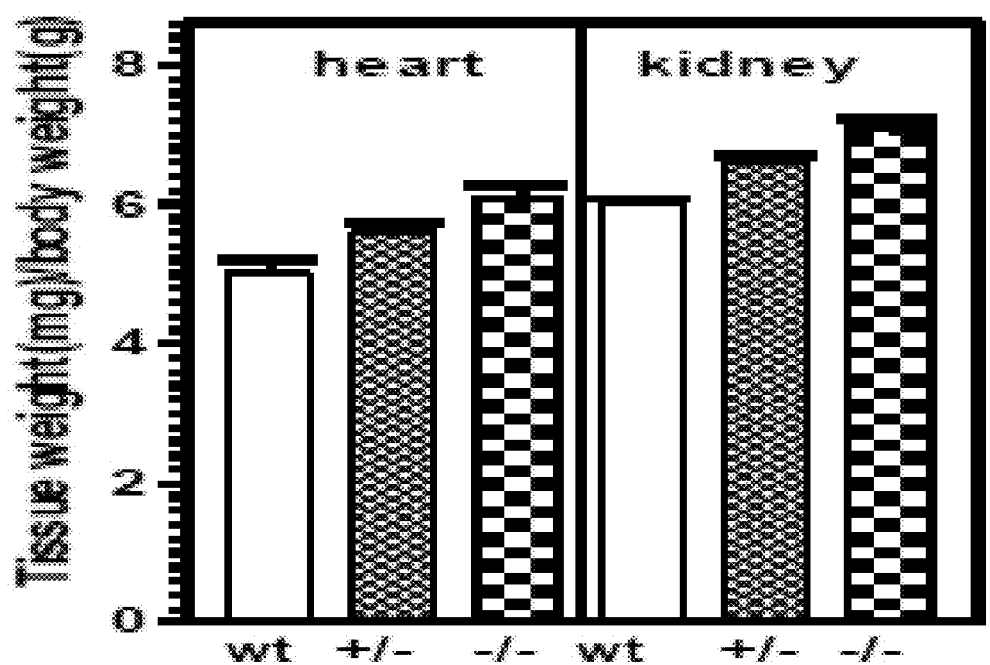
FIG. 3 illustrates the ratio of the heart or kidney weight (mg) to body weight (g) of 6 week old female wt, wildtype, ($^{669}$WTAPELL$^{675}$)+/− and ($^{669}$WTAPELL$^{675}$)−/− mice.

There was a significant difference in the ratio of heart or kidney weight to body weight between the mice with the $^{669}$WTAPELL$^{675}$ signaling null-motif and the control wt-ANF-RGC. FIG. 3 demonstrates the ratio of the heart or kidney weight (mg) to body weight (g) of 6 week old female wt, ($^{669}$WTAPELL$^{675}$)+/− and ($^{669}$WTAPELL$^{675}$)−/− mice. (Mean±SD of three measurements is provided). As illustrated, the number of ANF-RGC gene copies with the $^{669}$WTAPELL$^{675}$ motif deleted determined this ratio, which was 5±0.25 [0 copies (wt)] and 6.1±0.25 {2 copies ($^{669}$WTAPELL$^{675}$)−/−]} for the heart; 6.0±0.1 (0 copies) and 7.1±0.2 (2 copies) for the kidney (one kidney weight vs whole body weight). Thus, the cardiac and renal hypertrophy correlated with the loss of the encoded $^{669}$WTAPELL 1$^{675}$ motif of the ANF-RGC gene. The motif controls the ANF-dependent ANF-RGC activity for the generation of cyclic GMP.

What is claimed is:

1. A transgenic mouse whose genome comprises deletion of a nucleic acid sequence encoding an ATP-ST region comprising amino acid sequence WTAPELL (SEQ ID. NO.: 3) of an ANF-RGC protein, wherein the deletion diminishes ligand-stimulated production of cyclic GMP, as compared to a mouse having a wild-type genome.

2. The transgenic mouse of claim 1, wherein the deletion to the genome is heterozygous.

3. The transgenic mouse of claim 1, wherein the deletion to the genome is homozygous.

4. The transgenic mouse of claim 1, wherein, as compared to an mouse having a wildtype genome, the transgenic mouse exhibits reduced ligand-stimulated guanylate cyclase activity in a tissue selected from the group consisting of heart, kidney, adrenal gland, and combinations thereof.

5. The transgenic mouse of claim 4, wherein the transgenic mouse exhibits a reduction of greater than 50% ligand-stimulated guanylate cyclase activity in heart tissue.

6. The transgenic mouse of claim 4, wherein the transgenic mouse exhibits a reduction of greater than 50% ligand-stimulated guanylate cyclase activity in kidney tissue.

7. The transgenic mouse of claim 4, wherein the transgenic mouse exhibits a reduction of greater than 40% ligand-stimulated guanylate cyclase activity in adrenal gland tissue.

8. The transgenic mouse of claim 1, wherein the transgenic mouse exhibits renal or cardiac hypertrophy, as compared to a mouse having a wild-type genome.

9. The transgenic mouse of claim 8, wherein the transgenic mouse exhibits an increase in weight of greater than 5% in cardiac tissue.

10. The transgenic mouse of claim 8, wherein the transgenic mouse exhibits an increase in weight of greater than 5% in renal tissue.

11. The transgenic mouse of claim 1, wherein the transgenic mouse exhibits no change in basal guanylate cyclase activity.

12. A transgenic mouse whose genome comprises deletion of a nucleic acid sequence encoding an ATP-ST region comprising amino acid sequence WTAPELL (SEQ ID. NO.: 3) of an ANF-RGC protein, wherein, as compared to a mouse having a wild-type genome, the transgenic mouse exhibits reduced ANF-stimulated guanylate cyclase activity and exhibits no change in basal guanylate cyclase activity.

13. A cell line obtained from the transgenic mouse of claim 1.

* * * * *

SEQUENCE LISTING

<160> NUMBER OF SEQ ID NOS: 20

<210> SEQ ID NO 1
<211> LENGTH: 3171
<212> TYPE: DNA
<213> ORGANISM: Rattus norvegicus

<400> SEQUENCE: 1

```
atgccgggct cccgacgcgt ccgtccgcgc ctaagggcgc tgctgctgct gccgccgctt      60
ctgctactcc ggggcggcca cgcgagcgac ctgaccgtgg ctgtggtgct gccgctgacc     120
aacacctcgt acccgtggtc ctgggcgcgt gtagggccgg ccgtggaact ggctctcgcg     180
cgggtgaagg ctcggccgga cttgctgccg ggttggacgg tccgcatggt gctgggcagc     240
```

-continued

```
agtgagaacg cggcgggcgt ctgctcggac accgccgcac cgctggccgc ggtggacctc    300
aagtgggagc acagccccgc ggtgttcctg ggccccggct gcgtctactc cgctgccccg    360
gtggggcgct tcaccgcgca ctggcgggtg ccgctgctga ccgccggcgc cccggctctg    420
ggcatcgggg tcaaggatga gtatgcgcta accacccgca caggacccag ccatgtcaag    480 ctggcgatt tcgtgacggc gctgcatcga cggctgggct gggagcacca ggcgctggtg     540
ctctatgcag atcggctggg cgacgaccgg ccttgcttct tcatagtgga ggggctgtac    600
atgcgggtgc gtgaacgcct caacatcaca gtgaatcacc aggagttcgt cgagggcgac    660
ccggaccact accccaagct actgcgggcc gtgcggcgaa agggcagagt tatctacatc    720
tgcagttctc cggatgcctt caggaatctg atgcttctgg ccctgaacgc tggcctgact    780
ggggaggact atgttttctt ccacctggat gtgtttgggc aaagccttaa gagtgctcag    840
ggccttgttc cccagaaacc ctgggaaaga ggagatgggc aggacaggag tgcccgccaa    900 gccttcagg ctgccaaaat tattacttac aaagagcctg ataatcctga gtacttggaa     960
ttcctgaagc agctgaaact cttggctgac aagaagttca acttcaccgt ggaggatggc    1020
ctgaagaata tcatcccagc ctccttccac gacgggctcc tgctctatgt ccaggcagtg    1080
acagagactc tggcacacgg gggaactgtc acagatggag agaacatcac tcagcggatg    1140
tggaaccgaa gcttccaagg tgtgacagga tacccgaaaa ttgatagaaa cggagatcgg    1200
gacaccgatt tctctctctg ggatatggat ccagagacgg gtgccttcag ggttgtcctg    1260
aactataatg gtacttccca ggagctaatg gctgtgtcag aacacaaatt atactggcct    1320
ctgggatatc caccctcctga cgtccctaaa tgtggctttg acaatgagga cccagcctgc    1380
aaccaagacc acttttccac actggaggtt ctggctttgg tgggcagcct ctctctgatt    1440
agctttctga ttgtgtcttt cttcatatac aggaagatgc agctgaaaaa ggagctggtc    1500
tcagagttgt ggcgggtgcg ctgggaggac ttgcagccca gcagcctgga gaggcacctt    1560
cggagcgctg gcagccggct gacccctgagt gggcgaggct ccaattatgg ctccctgcta    1620
accaccgagg gccagttcca agtctttgcc aagacagcat actataaggg caaccttgtg    1680
gctgtgaaac gtgtgaaccg gaaacgcatt gagttgacac gaaaagtcct gtttgaactt    1740
aaacatatgc gggatgtgca gaatgaccac ttgacaagat ttgtgggtgc ttgtaccgac    1800 cccccccaaca tctgtatcct cacagagtac tgtccccgtg gaagcctaca ggacattcta    1860
gagaatgaga gtatcaccct ggactggatg tttcggtact cgctcaccaa tgacattgtc    1920
aagggaatgc tctttctaca caatggggcc atttgttccc atgggaacct caagtcatcc    1980
aactgtgtgg tagacgggcg cttcgtgtta aagatcacag actacggtct tgagagcttc    2040
agagacccgg agccagagca aggacacacc ctctttgcca aaaaattgtg gacggcacct    2100
gagctcctgc gaatggcttc gccacctgcc cgtggctccc aagctgggga tgtgtacagc    2160
tttggtatca tcctgcagga gattgcccta agaagtgggg tcttctatgt ggaaggtttg    2220
gacctcagcc caaagagat cattgagcgt gtgactcggg gtgagcagcc cccattccga    2280
ccctccatgg atctgcagag ccacctggag gaactggggc agctgatgca gcggtgctgg    2340
gcagaggacc cacaggagcg gccaccctttt cagcagatcc gctggcgct cgcaagttc    2400 aacaaggaga acagcagcaa catcctggac aacctgctgt cacgcatgga gcagtatgct    2460
aacaacctgg aggaactggt agaggagaga acacaagctt atctggagga gaagcgcaaa    2520
gctgaggcct tgctttacca gattctgcct cactccgtgg ctgagcagct gaagagaggc    2580
gagacagtcc aggctgaggc ctttgatagt gttaccatct acttcagtga tattgtgggc    2640
```

-continued

```
tttacagctc tttcagcaga aagcacaccc atgcaggtgg tgactctgct caatgatctg   2700
tacacctgtt ttgatgctgt catagacaac tttgatgtgt acaaggtgga gaccattggt   2760
gatgcttaca tggtggtgtc agggctccca gtgcggaatg gacaactcca cgcccgagag   2820
gtggcccgaa tggcacttgc actactggat gctgtgcgct ccttccgcat ccgccatagg   2880
ccccaggaac agctgcgctt gcgcattggc atccacacag gtcctgtgtg tgctggtgtg   2940
gtagggctaa agatgccccg atactgcctc tttggagaca cagtcaacac agcttcaaga   3000
atggagtcta atggagaagc cctcaagatc cacttgtctt cagagaccaa ggctgtgctg   3060
gaagagttcg atggtttcga gctggagctc cgaggggatg tggaaatgaa gggcaaaggc   3120
aaggttcgga cctattggct cctgggggag cggggatgta gcactcgagg c           3171
```

<210> SEQ ID NO 2
<211> LENGTH: 1057
<212> TYPE: PRT
<213> ORGANISM: Rattus norvegicus

<400> SEQUENCE: 2

```
Met Pro Gly Ser Arg Arg Val Arg Pro Arg Leu Arg Ala Leu Leu Leu
1               5                   10                  15

Leu Pro Pro Leu Leu Leu Arg Gly Gly His Ala Ser Asp Leu Thr
            20                  25                  30

Val Ala Val Leu Pro Leu Thr Asn Thr Ser Tyr Pro Trp Ser Tyr
        35                  40                  45

Ala Arg Val Gly Pro Ala Val Glu Leu Ala Leu Ala Arg Val Lys Ala
    50                  55                  60

Arg Pro Asp Leu Leu Pro Gly Trp Thr Val Arg Met Val Leu Gly Ser
65                  70                  75                  80

Ser Glu Asn Ala Ala Gly Val Cys Ser Asp Thr Ala Ala Pro Leu Ala
                85                  90                  95

Ala Val Asp Leu Lys Trp Glu His Ser Pro Ala Val Phe Leu Gly Pro
            100                 105                 110

Gly Cys Val Tyr Ser Ala Ala Pro Val Gly Arg Phe Thr Ala His Trp
        115                 120                 125

Arg Val Pro Leu Leu Thr Ala Gly Ala Pro Ala Leu Gly Ile Gly Val
    130                 135                 140

Lys Asp Glu Tyr Ala Leu Thr Thr Arg Thr Gly Pro Ser His Val Lys
145                 150                 155                 160

Leu Gly Asp Phe Val Thr Ala Leu His Arg Arg Leu Gly Trp Glu His
                165                 170                 175

Gln Ala Leu Val Leu Tyr Ala Asp Arg Leu Gly Asp Asp Arg Pro Cys
            180                 185                 190

Phe Phe Ile Val Glu Gly Leu Tyr Met Arg Val Arg Glu Arg Leu Asn
        195                 200                 205

Ile Thr Val Asn His Gln Glu Phe Val Glu Gly Asp Pro Asp His Tyr
    210                 215                 220

Pro Lys Leu Leu Arg Ala Val Arg Arg Lys Gly Arg Val Ile Tyr Ile
225                 230                 235                 240

Cys Ser Ser Pro Asp Ala Phe Arg Asn Leu Met Leu Leu Ala Leu Asn
                245                 250                 255

Ala Gly Leu Thr Gly Glu Asp Tyr Val Phe Phe His Leu Asp Val Phe
            260                 265                 270

Gly Gln Ser Leu Lys Ser Ala Gln Gly Leu Val Pro Gln Lys Pro Trp
```

-continued

```
              275                 280                 285
Glu Arg Gly Asp Gly Gln Asp Arg Ser Ala Arg Gln Ala Phe Gln Ala
290                 295                 300
Ala Lys Ile Ile Thr Tyr Lys Glu Pro Asp Asn Pro Glu Tyr Leu Glu
305                 310                 315                 320
Phe Leu Lys Gln Leu Lys Leu Ala Asp Lys Lys Phe Asn Phe Thr
                325                 330                 335
Val Glu Asp Gly Leu Lys Asn Ile Ile Pro Ala Ser Phe His Asp Gly
                340                 345                 350
Leu Leu Leu Tyr Val Gln Ala Val Thr Glu Thr Leu Ala His Gly Gly
                355                 360                 365
Thr Val Thr Asp Gly Glu Asn Ile Thr Gln Arg Met Trp Asn Arg Ser
370                 375                 380
Phe Gln Gly Val Thr Gly Tyr Pro Lys Ile Asp Arg Asn Gly Asp Arg
385                 390                 395                 400
Asp Thr Asp Phe Ser Leu Trp Asp Met Asp Pro Glu Thr Gly Ala Phe
                405                 410                 415
Arg Val Val Leu Asn Tyr Asn Gly Thr Ser Gln Glu Leu Met Ala Val
                420                 425                 430
Ser Glu His Lys Leu Tyr Trp Pro Leu Gly Tyr Pro Pro Asp Val
                435                 440                 445
Pro Lys Cys Gly Phe Asp Asn Glu Asp Pro Ala Cys Asn Gln Asp His
450                 455                 460
Phe Ser Thr Leu Glu Val Leu Ala Leu Val Gly Ser Leu Ser Leu Ile
465                 470                 475                 480
Ser Phe Leu Ile Val Ser Phe Ile Tyr Arg Lys Met Gln Leu Glu
                485                 490                 495
Lys Glu Leu Val Ser Glu Leu Trp Arg Val Arg Trp Glu Asp Leu Gln
                500                 505                 510
Pro Ser Ser Leu Glu Arg His Leu Arg Ser Ala Gly Ser Arg Leu Thr
                515                 520                 525
Leu Ser Gly Arg Gly Ser Asn Tyr Gly Ser Leu Leu Thr Thr Glu Gly
                530                 535                 540
Gln Phe Gln Val Phe Ala Lys Thr Ala Tyr Tyr Lys Gly Asn Leu Val
545                 550                 555                 560
Ala Val Lys Arg Val Asn Arg Lys Arg Ile Glu Leu Thr Arg Lys Val
                565                 570                 575
Leu Phe Glu Leu Lys His Met Arg Asp Val Gln Asn Glu His Leu Thr
                580                 585                 590
Arg Phe Val Gly Ala Cys Thr Asp Pro Pro Asn Ile Cys Ile Leu Thr
                595                 600                 605
Glu Tyr Cys Pro Arg Gly Ser Leu Gln Asp Ile Leu Glu Asn Glu Ser
                610                 615                 620
Ile Thr Leu Asp Trp Met Phe Arg Tyr Ser Leu Thr Asn Asp Ile Val
625                 630                 635                 640
Lys Gly Met Leu Phe Leu His Asn Gly Ala Ile Cys Ser His Gly Asn
                645                 650                 655
Leu Lys Ser Ser Asn Cys Val Val Asp Gly Arg Phe Val Leu Lys Ile
                660                 665                 670
Thr Asp Tyr Gly Leu Glu Ser Phe Arg Asp Pro Glu Pro Glu Gln Gly
                675                 680                 685
His Thr Leu Phe Ala Lys Lys Leu Trp Thr Ala Pro Glu Leu Leu Arg
                690                 695                 700
```

-continued

```
Met Ala Ser Pro Pro Ala Arg Gly Ser Gln Ala Gly Asp Val Tyr Ser
705                 710                 715                 720

Phe Gly Ile Ile Leu Gln Glu Ile Ala Leu Arg Ser Gly Val Phe Tyr
            725                 730                 735

Val Glu Gly Leu Asp Leu Ser Pro Lys Glu Ile Ile Glu Arg Val Thr
        740                 745                 750

Arg Gly Glu Gln Pro Pro Phe Arg Pro Ser Met Asp Leu Gln Ser His
            755                 760                 765

Leu Glu Glu Leu Gly Gln Leu Met Gln Arg Cys Trp Ala Glu Asp Pro
        770                 775                 780

Gln Glu Arg Pro Pro Phe Gln Gln Ile Arg Leu Ala Leu Arg Lys Phe
785                 790                 795                 800

Asn Lys Glu Asn Ser Ser Asn Ile Leu Asp Asn Leu Leu Ser Arg Met
            805                 810                 815

Glu Gln Tyr Ala Asn Asn Leu Glu Glu Leu Val Glu Glu Arg Thr Gln
        820                 825                 830

Ala Tyr Leu Glu Glu Lys Arg Lys Ala Glu Ala Leu Leu Tyr Gln Ile
            835                 840                 845

Leu Pro His Ser Val Ala Glu Gln Leu Lys Arg Gly Glu Thr Val Gln
850                 855                 860

Ala Glu Ala Phe Asp Ser Val Thr Ile Tyr Phe Ser Asp Ile Val Gly
865                 870                 875                 880

Phe Thr Ala Leu Ser Ala Glu Ser Thr Pro Met Gln Val Val Thr Leu
            885                 890                 895

Leu Asn Asp Leu Tyr Thr Cys Phe Asp Ala Val Ile Asp Asn Phe Asp
        900                 905                 910

Val Tyr Lys Val Glu Thr Ile Gly Asp Ala Tyr Met Val Val Ser Gly
            915                 920                 925

Leu Pro Val Arg Asn Gly Gln Leu His Ala Arg Glu Val Ala Arg Met
930                 935                 940

Ala Leu Ala Leu Leu Asp Ala Val Arg Ser Phe Arg Ile Arg His Arg
945                 950                 955                 960

Pro Gln Glu Gln Leu Arg Leu Arg Ile Gly Ile His Thr Gly Pro Val
            965                 970                 975

Cys Ala Gly Val Val Gly Leu Lys Met Pro Arg Tyr Cys Leu Phe Gly
        980                 985                 990

Asp Thr Val Asn Thr Ala Ser Arg Met Glu Ser Asn Gly Glu Ala Leu
            995                 1000                1005

Lys Ile His Leu Ser Ser Glu Thr Lys Ala Val Leu Glu Glu Phe
    1010                1015                1020

Asp Gly Phe Glu Leu Glu Leu Arg Gly Asp Val Glu Met Lys Gly
    1025                1030                1035

Lys Gly Lys Val Arg Thr Tyr Trp Leu Leu Gly Glu Arg Gly Cys
    1040                1045                1050

Ser Thr Arg Gly
    1055

<210> SEQ ID NO 3
<211> LENGTH: 7
<212> TYPE: PRT
<213> ORGANISM: Artificial
<220> FEATURE:
<223> OTHER INFORMATION: ARM portion of synthetic ANF-RGC protein

<400> SEQUENCE: 3
```

Trp Thr Ala Pro Glu Leu Leu
1               5

<210> SEQ ID NO 4
<211> LENGTH: 3171
<212> TYPE: DNA
<213> ORGANISM: Mus musculus

<400> SEQUENCE: 4

```
atgccgcgtt cccgacgcgt ccgtccgcgc ctaagggcgc tgctgctgct accgccgctg      60
ctgctgctcc gaagcggcca cgcgagcgac ctgaccgtgg ctgtggtgct gcccgtgacc     120
aacacctcgt acccgtggtc ctgggcgcgt gtagggccgg cggtggaact ggctctcggg     180
agggtgaagg ctcggccgga cttgctgccg ggttggacgg tccgtatggt gctgggcagc     240
agcgagaacg cggcgggcgt ctgctccgac accgctgcac cgctggccgc ggtggatctc     300
aagtgggagc acagccccgc cgtgttcctg ggccccggct gcgtatactc tgctgccccg     360
gtggaccgct tcaccgcgca ctggcggttg ccgctgctga cggctggcgc cccggctctg     420
ggcatcgggg tgaaggatga gtacgcgtta accacccgca caggacccag ccatgtcaag     480
ctgggcgact tcgtgacggc gctgcatcga cggctgggct gggagcacca ggcgcttgtg     540
ctctatgcag atcggctggg cgacgaccgg ccgtgcttct tcatagtgga ggggctgtac     600
atgcgggtgc gtgagcgact caacatcaca gtaaatcacc aggagttcgt cgagggcgac     660
ccggaccact acaccaagct actgcggacc gtgcagcgca agggcagagt tatctacatc     720
tgcagttctc cggatgcctt caggaatctg atgcttttgg ccctggatgc tggcctgact     780
ggggaggact atgttttctt ccacctggat gtgtttgggc aaagccttca gggtgctcag     840
ggccctgttc cagagaagcc ctgggaaaga cgatgggc aggataggag agcccgccag     900
cgctttcagg ctgcaaaaat tattacttac aaagaacccg ataatcctga gtacttggaa     960
ttcctgaagc agctaaaact cttggctgac aagaaattca acttcaccat ggaggatggc    1020
ctgaaaaata tcatcccagc atccttccat gacgggctcc tgctctatgt ccaggcagtg    1080
acagagactc tggcacaggg gggcactgtc actgatggag agaacatcac tcagcggatg    1140
tggaaccgaa gcttccaagg tgtgacagga tacctgaaaa ttgatagaaa tggagatcgg    1200
gacactgatt ctcctctctg ggatatggac cccgagacag gtgccttcag ggttgtcctg    1260
aactttaatg gtacttccca ggagctgatg gctgtgtcag aacacagatt atactggcct    1320
ctgggatacc cacctcctga catccctaaa tgtggctttg acaatgagga cccagcctgc    1380
aaccaagacc acttttccac actggaggtt ctggctttgg tgggcagcct ctctctggtt    1440
agctttctga tcgtgtcttt cttcatatac aggaagatgc agctggaaaa ggagctggtc    1500
tcagagttgt ggcgggtgcg ctgggaggac ttgcagccca gcagcctgga gaggcacctt    1560
cggagcgctg gcagtcggct gaccctgagt gggcgaggct ccaattatgg ctccctgcta    1620
accacggagg gccagttcca agtctttgcc aagacagcat actataaggg caacctcgtg    1680
gctgtgaaac gtgtgaaccg gaaacgcatt gagttgacac gaaaagtcct gtttgaactt    1740
aaacatatgc gggatgtgca gaatgagcaa ttgaccagat tgtgggagc ttgtaccgac    1800
cctcccaaca tctgtatcct cacagagtac tgtccccgtg gaagcctaca ggacattcta    1860
gagaatgaga gtattaccct ggactggatg tttcggtact cactcaccaa tgacattgtc    1920
aagggaatgc tctttctaca caacgggccc atttgttccc atgggaacct caagtcatcc    1980
aactgcgtgg tagatggacg ttttgtgtta aagatcacag actatgggct cgagagcttc    2040
```

| | | |
|---|---|---|
| agagacccgg agccagagca aggacacacc ctctttgcca aaaaactgtg gactgcacct | 2100 | |
| gagctcctgc gaatggcttc cccacctgcc cgtggctccc aagctgggga tgtctacagt | 2160 | |
| tttggtatca tccttcagga aattgcccta agaagtgggg tcttctatgt ggaaggtttg | 2220 | |
| gacctcagcc caaagagat cattgagcgt gtgactcggg gtgagcagcc cccattccga | 2280 | |
| ccttccatgg atctgcagag ccacctggag gaactggggc agctgatgca gaggtgctgg | 2340 | |
| gcagaggatc ctcaggagcg gccacccttt caacagatcc gcctggcgct gcgcaagttc | 2400 | |
| aacaaggaga acagcagcaa catcctggac aacctgctgt cacgcatgga acagtacgcc | 2460 | |
| aacaacctgg aggaactggt agaggagaga acacagcctt atctggagga aagcgcaaa | 2520 | |
| gctgaggccc tgctttacca gattctgcct cactctgtgg ctgagcagct aagagaggc | 2580 | |
| gagacagtcc aggctgaggc atttgatagt gttactatct atttcagtga tatcgtgggc | 2640 | |
| tttacagctc tttcagcaga gagcacaccc atgcaggtgg tcaccctgct caatgatctg | 2700 | |
| tacacctgtt ttgatgctgt catagacaac tttgatgtgt acaaggtaga gaccattggt | 2760 | |
| gatgcttaca tggtggtatc agggctccca gtgaggaatg gacagctcca tgcccgagag | 2820 | |
| gtagcccgaa tggcacttgc actgctcgat gctgtacgct ccttccgcat cggccatagg | 2880 | |
| ccccaggaac agctgcgctt gcgcattgga attcacacag tcctgtgtg tgctggtgtg | 2940 | |
| gtagggctaa agatgccccg atactgcctc tttggagaca cagtcaacac agcttcaaga | 3000 | |
| atggagtcta atggggaagc cctcaggatc cacttgtctt cggagaccaa ggctgtgctg | 3060 | |
| gaagagttcg atggtttcga gctggagctc cgaggggatg tggaaatgaa gggcaaaggc | 3120 | |
| aaggttcgtt cctattggct cctcggggac cggggatgca gctctcgagc c | 3171 | |

<210> SEQ ID NO 5
<211> LENGTH: 940
<212> TYPE: PRT
<213> ORGANISM: Mus musculus

<400> SEQUENCE: 5

Met Pro Arg Ser Arg Val Arg Pro Arg Leu Arg Ala Leu Leu Leu
1               5                   10                  15

Leu Pro Pro Leu Leu Leu Arg Ser Gly His Ala Ser Asp Leu Thr
            20                  25                  30

Val Ala Val Val Leu Pro Val Thr Asn Thr Ser Tyr Pro Trp Ser Trp
        35                  40                  45

Ala Arg Val Gly Pro Ala Val Glu Leu Ala Leu Gly Arg Val Lys Ala
    50                  55                  60

Arg Pro Asp Leu Leu Pro Gly Trp Thr Val Arg Met Val Leu Gly Ser
65                  70                  75                  80

Ser Glu Asn Ala Ala Gly Val Cys Ser Asp Thr Ala Ala Pro Leu Ala
                85                  90                  95

Ala Val Asp Leu Lys Trp Glu His Ser Pro Ala Val Phe Leu Gly Pro
            100                 105                 110

Gly Cys Val Tyr Ser Ala Ala Pro Val Asp Arg Phe Thr Ala His Trp
        115                 120                 125

Arg Leu Pro Leu Leu Thr Ala Gly Ala Pro Ala Leu Gly Ile Gly Val
    130                 135                 140

Lys Asp Glu Tyr Ala Leu Thr Thr Arg Thr Gly Pro Ser His Val Lys
145                 150                 155                 160

Leu Gly Asp Phe Val Thr Ala Leu His Arg Arg Leu Gly Trp Glu His
                165                 170                 175

```
Gln Ala Leu Val Leu Tyr Ala Asp Arg Leu Gly Asp Arg Pro Cys
            180                 185                 190

Phe Phe Ile Val Glu Gly Leu Tyr Met Arg Val Arg Glu Arg Leu Asn
        195                 200                 205

Ile Thr Val Asn His Gln Glu Phe Val Glu Gly Asp Pro Asp His Tyr
    210                 215                 220

Thr Lys Leu Leu Arg Thr Val Gln Arg Lys Gly Arg Val Ile Tyr Ile
225                 230                 235                 240

Cys Ser Ser Pro Asp Ala Phe Arg Asn Leu Met Leu Leu Ala Leu Asp
                245                 250                 255

Ala Gly Leu Thr Gly Glu Asp Tyr Val Phe Phe His Leu Asp Val Phe
            260                 265                 270

Gly Gln Ser Leu Gln Gly Ala Gln Gly Pro Val Pro Glu Lys Pro Trp
        275                 280                 285

Glu Arg Asp Asp Gly Gln Asp Arg Arg Ala Arg Gln Arg Phe Gln Ala
    290                 295                 300

Ala Lys Ile Ile Thr Tyr Lys Glu Pro Asp Asn Pro Glu Tyr Leu Glu
305                 310                 315                 320

Phe Leu Lys Gln Leu Lys Leu Ala Asp Lys Lys Phe Asn Phe Thr
                325                 330                 335

Met Glu Asp Gly Leu Lys Asn Ile Ile Pro Ala Ser Phe His Asp Gly
            340                 345                 350

Leu Leu Leu Tyr Val Gln Ala Val Thr Glu Thr Leu Ala Gln Glu Glu
        355                 360                 365

Thr Val Thr Asp Gly Glu Asn Ile Thr Gln Arg Met Trp Asn Arg Ser
    370                 375                 380

Phe Gln Glu Val Thr Gly Tyr Leu Lys Ile Asp Arg Asn Gly Asp Arg
385                 390                 395                 400

Asp Thr Asp Ser Pro Leu Trp Asp Met Asp Pro Glu Thr Gly Ala Phe
                405                 410                 415

Arg Val Val Leu Asn Phe Asn Gly Thr Ser Gln Glu Leu Met Ala Val
            420                 425                 430

Ser Glu His Arg Leu Tyr Trp Pro Leu Gly Tyr Pro Pro Pro Asp Ile
        435                 440                 445

Pro Lys Cys Gly Phe Asp Asn Glu Asp Pro Ala Cys Asn Gln Asp His
    450                 455                 460

Phe Ser Thr Leu Glu Val Leu Ala Leu Val Gly Ser Leu Ser Leu Val
465                 470                 475                 480

Ser Phe Leu Ile Val Ser Phe Phe Ile Tyr Arg Lys Met Gln Leu Glu
                485                 490                 495

Lys Glu Leu Val Ser Glu Leu Trp Arg Val Arg Trp Glu Asp Leu Gln
            500                 505                 510

Pro Ser Ser Leu Glu Arg His Leu Arg Ser Ala Gly Ser Arg Leu Thr
        515                 520                 525

Leu Ser Gly Arg Gly Ser Asn Tyr Gly Ser Leu Leu Thr Thr Glu Gly
    530                 535                 540

Gln Phe Gln Val Phe Ala Lys Thr Ala Tyr Tyr Lys Gly Asn Leu Val
545                 550                 555                 560

Ala Val Lys Arg Val Asn Arg Lys Arg Ile Glu Leu Thr Arg Lys Val
                565                 570                 575

Leu Phe Glu Leu Lys His Met Arg Asp Val Gln Asn Glu Gln Leu Thr
            580                 585                 590
```

| | | | | | | | | | | | | |
|---|---|---|---|---|---|---|---|---|---|---|---|---|
|Arg|Phe|Val|Gly|Ala|Cys|Thr|Asp|Pro|Pro|Asn|Ile|Cys|Ile|Leu|Thr|
| | |595| | | |600| | | |605| | | | | |

Glu Tyr Cys Pro Arg Gly Ser Leu Gln Asp Ile Leu Glu Asn Glu Ser
          610             615             620

Ile Thr Leu Asp Trp Met Phe Arg Tyr Ser Leu Thr Asn Asp Ile Val
625             630             635             640

Lys Gly Met Leu Phe Leu His Asn Gly Ala Ile Cys Ser His Gly Asn
              645             650             655

Leu Lys Ser Ser Asn Cys Val Val Asp Gly Arg Phe Val Leu Lys Ile
          660             665             670

Thr Asp Tyr Gly Leu Glu Ser Phe Arg Asp Pro Glu Pro Glu Lys Glu
      675             680             685

Ile Ile Glu Arg Val Thr Arg Gly Glu Gln Pro Pro Phe Lys Phe Asn
      690             695             700

Lys Glu Asn Ser Ser Asn Ile Leu Asp Asn Leu Leu Ser Arg Met Glu
705             710             715             720

Asn Leu Arg Leu Glu Ala Leu Leu Tyr Gln Ile Leu Pro His Ser Val
              725             730             735

Ala Glu Gln Leu Lys Arg Gly Glu Thr Val Gln Ala Glu Ala Phe Asp
          740             745             750

Ser Val Thr Ile Tyr Phe Ser Asp Ile Val Gly Phe Thr Ala Leu Ser
      755             760             765

Ala Glu Ser Thr Phe Met Gln Val Val Thr Leu Leu Asn Asp Leu Tyr
770             775             780

Thr Cys Phe Asp Ala Val Ile Asp Asn Phe Asp Val Tyr Lys Val Glu
785             790             795             800

Thr Ile Gly Asp Ala Tyr Met Val Val Ser Gly Leu Pro Val Arg Asn
              805             810             815

Gly Gln Leu His Ala Arg Glu Val Ala Arg Met Ala Leu Ala Leu Leu
          820             825             830

Asp Ala Val Arg Ser Phe Arg Ile Gly His Arg Pro Gln Glu Gln Leu
      835             840             845

Arg Leu Arg Ile Gly Ile His Thr Gly Pro Val Cys Ala Gly Val Val
850             855             860

Gly Leu Lys Met Pro Arg Tyr Cys Leu Phe Gly Asp Thr Val Asn Thr
865             870             875             880

Ala Ser Arg Met Glu Ser Asn Gly Glu Ala Leu Arg Ile His Ile Ser
              885             890             895

Ser Glu Thr Lys Ala Val Leu Glu Phe Asp Gly Phe Asp Leu Glu
          900             905             910

Leu Arg Gly Asp Val Glu Met Lys Gly Lys Gly Lys Val Arg Ser Tyr
      915             920             925

Trp Leu Leu Gly Asp Arg Gly Cys Ser Ser Arg Ala
930             935             940

<210> SEQ ID NO 6
<211> LENGTH: 2065
<212> TYPE: DNA
<213> ORGANISM: Mus musculus

<400> SEQUENCE: 6
ggctgatgag ttagcggaag cttctagatg aggtgactca cccggaccca ggacttgggt    60
ggttaagata ggaagatctt gctgtaagtc tgaggctagc ccatccgtct ctcataaaac   120
cagagccaaa caaaagaaca ggctaacccc cagctctgcc ttcacttgct cactctgaca   180

```
ttgtcttaag tgagggttgc agttacagcc tctgtaacaa ggccctctca aaggtcaaat        240
gacatagtct aagtaagcac gcaggtatga gtcaatacca ctacacaaag gcgggtggga        300
gctggcatgg gtagcttaca cctgcaatca ttactacaag ttcaggcaac cctgagctaa        360
agagtgagag cctctctctg caaggtaaca gataaagggg cagttgtgat tgaatctaga        420
acttccagga tgcagaaatg acctctgggc tgaccaatag atgactattg ttcatctctg        480
tagcgagcgt ccaattatgg ctccctgcta accacgcgagg gccagttcca agtctttgcc        540
aagacagcat actataaggt aggtctgggg caagattgta gagtgtgctc tgaggactaa        600
gagatggttc tgagtgggct gccagggaca ggggtggtcc cagggcaggg tgggcttttta       660 gaagcaggta gagagctggg gtcatggatg ggtttcagaa gcagatggga gtctcaggtc        720
atctcctgaa taataagttt ccatttcttg ctcagggcaa cctcgtggct gtgaaacgtg        780
tgaaccggaa acgcattgag ttgacacgaa aagtcctgtt tgaacttaaa catgttaatt        840
tacgggggaa caaggctgtg gcttgggaaa gggccccatg ggtactccca agagagtcgg        900
ccaacagaac ttgattatgg aaggatctat acatctggga tgggcccttg agtcttgtgg        960
gtaggaaaaa ggagatcagt catgagagat cactgggtcc tccagggtcc agacgggttg        1020
tcctcatagg tacagccagg aaatcaaggg gttagggagc agatgctgag aaagaatgtt        1080
aatcaacaca tgacttggtg aggtatgaag cctctgccag gccttgatgc tgcccccact        1140
tgcagatgcg ggatgtgcag aatgagcact tgaccagatt tgtgggagct tgtaccgacc        1200
ctcccaacat ctgtatcctc acagagtact gtccccgtgg gagcctacag gtgagcggga        1260
caagagggag tgtgtcgaga agcccggggt tccagccctg gctcttaccc cattgatcac        1320
atgagcccag ataagcttcc tctttctggc cattcttggc ctctctgtaa atggggggttg       1380 ggggcgggca tggcactaca gcaaatccaa agtgtccaag cttacgccag tagctcccctt      1440 gctaccctcc tcctgactcc caagggggggt ctgactcctt gcttccccca gcaggacatt      1500
ctagagaatg agagtattac cctggactgg atgtttcggt actcactcac caatgacatt       1560
gtcaaggtga gtcccagagg agctcaactg gatgccaggc aagggctggg catggttgga       1620
agtcacgaac ccgagccctc tcgccttcct aaatattcca gggaatgctc tttctacaca       1680
acggggccat tggttcccat gggaacctca agtcatccaa ctgcgtggta gatggacgtt       1740
ttgtgttaaa gatcacagac tatgggctcg agagcttcag agacccggag ccagagcaag       1800
gacacaccct cttttgccagt aagtctgact cttgaccccta ggcctctgct gccaacacaa     1860
gctcagaagg gaaactgagg cctaacctct gcatgacttg ggtataccctc tcatctgcaa      1920 ggctcaatct tcattggttt aaaaaggagg tcagaccaag tggtcactgg gttctcagca       1980
ctgtgccgtg tgccacagga gtccctagct acacccttga tccctgatta tcttaaacca       2040
tatgacaagc ttatttttcg cagcc                                             2065
```

<210> SEQ ID NO 7
<211> LENGTH: 2470
<212> TYPE: DNA
<213> ORGANISM: Mus musculus

<400> SEQUENCE: 7

```
ttctcagaat tatcacacca tcctgtctta cttttttttt catttaaata tttatttatt        60
tatttcctgc atagttgaat acatcattgc tctgcttcag acacagcaag aaggagggca       120
tcagaatctc attacccaga tgatcgtgag ccaccatgtg gttgctggga attgaactca       180
```

```
ggacctctag aagagcagtc agtgttctta accactgagc tatttttcca ggcccccacc    240
cctgtcttac ttttattata gcatttatta cccatgaaat ataatattca tttgctagtt    300 tttcttttc ccatcataat gtaaagtccc ttatcccttc tatgactccc aacctctgat    360
ccacagaaaa actgtggact gcacctgagc tcctgcgaat ggcttcccca cctgcccgtg    420
gctcccaagc tggggatgtc tacagttttg gtatcatcct tcaggaaatt gccctaagaa    480
gtggggtctc ctatgtggaa ggtttggacc tcagcccaaa aggtgaggat cacttggcct    540 atacccagc caatcttgat gaatctacca ccagagaggg aacctctcca aacacccta     600 ccattcctc tggagtgggg agtcagccac tatcctttgc tctgtggctg ctagtgacca    660
gtccactctg tgctctggtc tggacttgtc ccacctagac aggtctatcc cagctggttg    720
cccagctagg cttgccgctc ttcagtgcgt gccccttcca cacagagatc attgagcgtg    780
tgactcgggg cgagcagccc ccattccgac cttccatgga tctgcagagc cacctggagg    840
aactggggca gctgatgcag aggtgctggg cagaggatcc tcaggagcgg ccaccctttc    900
aacagatccg cctggcgctg cgcaagttca acaagttagt ggtctctccc actacaacca    960
ctgtaaatcc cacacttaaa tcttcttcta cagtggcagc ccacagaagc caccacagcc   1020
tcaaaggcat ctgcatagct ggatgacttg gctgtcccaa cagctcctta ccattcacta   1080
ctccttcctc tgccaacatt gatacccac acccttcct gcccacggcc ctgtactaac    1140
ccccagactt ccatctcttt tttccagtat gcccaccggc tagttctccc actcatgtct   1200
ctctgctgcc tgtcactatc ctcagctcac cctgcttctc tccctcccca cctccttcaa   1260
actcacttgt gttcaataag aataagtaag aactccagct ggtcagagaa gcaggtagat   1320
gtctgtgggt tcaaggccag ttgttctttt cacctaaaac ccctgataat gtgaatagat   1380
ccagctatgg ctacctagag agaccctgtc tttaagggtg gggcaggcat ggtgagtgcc   1440
tgaataatgt gggcactgcc aggaagaacc agtcatccca tctcatctca tctgctcccc   1500
ccgccccccg cccctgtaac ccatggccct caggagaac agcagcaaca ccctggacaa    1560
cctgctgtca cgcatggaac agtacgccaa caacctggag gaactggtag aggagagaac   1620
acaggcttat ctggaggaga gcgcaaagc tgaggccctg ctttaccaga ttctgcctca   1680
gtgagttcta aactctgcac gcgcgcgcgc gcgcgcgcgc gcacacacac acacacacac   1740
acacacacac acacacacac aaacgtatag ccctgtcccc atcccatctc acctcttggt   1800
ctctacctgc cctctcccct cagctctgtg gctgagcagc tgaagagagg cgagacagtc   1860
caggctgagg catttgatag tgttactatc tatttcagtg atatcgtggg ctttacagct   1920 cttttcagcag agagcacacc catgcaggta agccggggtt cagccacagc aacaggccag   1980
gtaggtcagc ttgccacctg gttagtactc tccacttgtc cctggtggga ccctcattc    2040 accatttctc ttggcttcct ttgccttcca ggtggtcacc ctgctcaatg atctgtacac   2100 ctgtttgat gctgtcatag acaactttga tgtgtacaag gtgaggttat gagtagagac   2160
aagaaagaca ggcagacatg gacagtcaga aaatgttcag agggatcctc tgaaacaaac   2220
aaaacaaaac aaaaaaggcc aggcatggtg gtgcacacct ttaatcctac cacttgaaga   2280
tagatgcagg gaaatctatg agtttgaggc cagcctgagc aagtttcagg acaggacccc   2340
atagctacac tcaaagaaac tctgtcttga aaaacaaag gagaagaagg aagaggagga   2400
ggaggagaaa ggggaggaag aagaggagga ggagaaggag gagaaggaag aagaagaagg   2460
agaaggaaga                                                          2470
```

```
<210> SEQ ID NO 8
<211> LENGTH: 30
<212> TYPE: DNA
<213> ORGANISM: Artificial
<220> FEATURE:
<223> OTHER INFORMATION: Synthetic primer

<400> SEQUENCE: 8
ggctgatgag ttagcggaag cttctagatg                                    30

<210> SEQ ID NO 9
<211> LENGTH: 30
<212> TYPE: DNA
<213> ORGANISM: Artificial
<220> FEATURE:
<223> OTHER INFORMATION: Synthetic primer

<400> SEQUENCE: 9
ggctgcgaaa aataagcttg tcatatggtt                                    30

<210> SEQ ID NO 10
<211> LENGTH: 30
<212> TYPE: DNA
<213> ORGANISM: Artificial
<220> FEATURE:
<223> OTHER INFORMATION: Synthetic primer

<400> SEQUENCE: 10
ttctcagaat tatcacacca tcctgtctta                                    30

<210> SEQ ID NO 11
<211> LENGTH: 30
<212> TYPE: DNA
<213> ORGANISM: Artificial
<220> FEATURE:
<223> OTHER INFORMATION: Synthetic primer

<400> SEQUENCE: 11
tcttccttct ccttcttctt cttccttctc                                    30

<210> SEQ ID NO 12
<211> LENGTH: 35
<212> TYPE: DNA
<213> ORGANISM: Artificial
<220> FEATURE:
<223> OTHER INFORMATION: LoxP

<400> SEQUENCE: 12
ataacttcgt ataatgttat gctatacgaa gttat                              35

<210> SEQ ID NO 13
<211> LENGTH: 30
<212> TYPE: DNA
<213> ORGANISM: Artificial
<220> FEATURE:
<223> OTHER INFORMATION: Synthetic primer

<400> SEQUENCE: 13
agaggcacct tcggagcgct ggcagtcggc                                    30

<210> SEQ ID NO 14
<211> LENGTH: 30
<212> TYPE: DNA
<213> ORGANISM: Artificial
<220> FEATURE:
<223> OTHER INFORMATION: Synthetic primer
```

<400> SEQUENCE: 14
ctgggagccc tgataccacc atgtaagcat                                              30

<210> SEQ ID NO 15
<211> LENGTH: 9
<212> TYPE: PRT
<213> ORGANISM: Artificial
<220> FEATURE:
<223> OTHER INFORMATION: ARM region of synthetic ANF-RGC protein

<400> SEQUENCE: 15

Ser Ser Asn Cys Val Val Asp Gly Arg
1               5

<210> SEQ ID NO 16
<211> LENGTH: 7
<212> TYPE: PRT
<213> ORGANISM: Artificial
<220> FEATURE:
<223> OTHER INFORMATION: ARM region of synthetic ANF-RGC protein

<400> SEQUENCE: 16

Gly Arg Gly Ser Asn Tyr Gly
1               5

<210> SEQ ID NO 17
<211> LENGTH: 8
<212> TYPE: PRT
<213> ORGANISM: Artificial
<220> FEATURE:
<223> OTHER INFORMATION: ARM region of synthetic ANF-RGC protein

<400> SEQUENCE: 17

Val Lys Ile Gly Asp Phe Gly Met
1               5

<210> SEQ ID NO 18
<211> LENGTH: 3183
<212> TYPE: DNA
<213> ORGANISM: Homo sapiens

<400> SEQUENCE: 18
atgccggggc ccggcgcccc gctggctcc cgcctgcgcc tgctcctgct cctgctgctg        60
ccgccgctgc tgctgctgct ccggggcagc cacgcgggca acctgacggt agccgtggta       120
ctgccgctgg ccaataccctc gtaccccctg tcgtgggcgc gcgtgggacc cgccgtggag      180 ctggcccctgg cccaggtgaa ggcgcgcccc gacttgctgc cgggctggac ggtccgcacg      240
gtgctgggca gcagcgaaaa cgcgctgggc gtctgctccg acaccgcagc gccctggcc        300 gcggtggacc tcaagtggga gcacaacccc gctgtgttcc tgggcccgg ctgcgtgtac        360 gccgccgccc cagtggggcg cttcaccgcg cactggcggg tcccgctgct gaccgccggc       420
gccccggcgc tgggcttcgg tgtcaaggac gagtatgcgc tgaccaccccg cgcggggccc      480 agctacgcca agctggggga cttcgtggcg gcgctgcacc gacggctggg ctgggagcgc       540
caagcgctca tgctctacgc ctaccggccg ggtgacgaag agcactgctt cttcctcgtg       600
gaggggctgt tcatgcgggt ccgcgaccgc ctcaatatta cggtggacca cctggagttc       660
gccgaggacg acctcagcca ctacaccagg ctgctgcgga ccatgccgcg caaaggccga       720
gttatctaca tctgcagctc ccctgatgcc ttcagaaccc tcatgctcct ggccctggaa       780 gctggccttgt gtggggagga ctacgttttc ttccacctgg atatctttgg gcaaagcctg       840

```
caaggtggac agggccctgc tccccgcagg ccctgggaga gaggggatgg gcaggatgtc    900
agtgcccgcc aggcctttca ggctgccaaa atcattacat ataaagaccc agataatccc    960
gagtacttgg aattcctgaa gcagttaaaa cacctggcct atgagcagtt caacttcacc   1020
atggaggatg gcctggtgaa caccatccca gcatccttcc acgacgggct cctgctctat   1080
atccaggcag tgacggagac tctggcacat gggggaactg ttactgatgg ggagaacatc   1140
actcagcgga tgtggaaccg aagctttcaa ggtgtgacag gatacctgaa aattgatagc   1200
agtggcgatc gggaaacaga cttctccctc tgggatatgg atcccgagaa tggtgccttc   1260
agggttgtac tgaactacaa tgggacttcc caagagctgg tggctgtgtc ggggcgcaaa   1320
ctgaactggc ccctggggta ccctcctcct gacatcccca atgtggcttt tgacaacgaa   1380
gacccagcat gcaaccaaga tcaccttttcc accctggagg tgctggcttt ggtgggcagc   1440
ctctccttgc tcggcattct gattgtctcc ttcttcatat acaggaagat gcagctggag   1500
aaggaactgg cctcggagct gtggcgggtg cgctgggagg acgttgagcc cagtagcctt   1560
gagaggcacc tgcggagtgc aggcagccgg ctgacccctga gcgggagagg ctccaattac   1620
ggctccctgc taaccacaga gggccagttc caagtctttg ccaagacagc atattataag   1680
ggcaacctcg tggctgtgaa acgtgtgaac cgtaaacgca ttgagctgac acgaaaagtc   1740
ctgtttgaac tgaagcatat gcgggatgtg cagaatgaac acctgaccag gtttgtggga   1800
gcctgcaccg acccccccaa tatctgcatc ctcacagagt actgtcccg tgggagcctg   1860
caggacattc tggagaatga gagcatcacc ctggactgga tgttccggta ctcactcacc   1920
aatgacatcg tcaagggcat gctgtttcta cacaatgggg ctatctgttc ccatgggaac   1980
ctcaagtcat ccaactgcgt ggtagatggg cgctttgtgc tcaagatcac cgactatggg   2040
ctggagagct tcagggacct ggacccagag caaggacaca ccgtttatgc caaaaagctg   2100
tggacggccc ctgagctcct gcgaatggct tcacccccctg tgcggggctc ccaggctggt   2160
gacgtataca gctttgggat catccttcag gagattgccc tgaggagtgg ggtcttccac   2220
gtggaaggtt tggacctgag ccccaaagag atcatcgagc gggtgactcg gggtgagcag   2280
ccccccttcc ggccctccct ggccctgcag agtcacctgg aggagttggg gctgctcatg   2340
cagcggtgct gggctgagga cccacaggag aggccaccat tccagcagat ccgcctgacg   2400
ttgcgcaaat ttaacaggga gaacagcagc aacatcctgg acaacctgct gtcccgcatg   2460
gagcagtacg cgaacaatct ggaggaactg gtggaggagc ggacccaggc ataccctggag   2520
gagaagcgca aggctgaggc cctgctctac cagatcctgc ctcactcagt ggctgagcag   2580
ctgaagcgtg gggagacggt gcaggccgaa gcctttgaca gtgttaccat ctacttcagt   2640
gacattgtgg gtttcacagc gctgtcggcg gagagcacac ccatgcaggt ggtgaccctg   2700
ctcaatgacc tgtacacttg ctttgatgct gtcatagaca actttgatgt gtacaaggtg   2760
gagacaattg gcgatgccta catggtggtc tcagggctcc ctgtgcggaa cgggcggcta   2820
cacgcctgcg aggtagcccg catggccctg gcactgctgg atgctgtgcg ctccttccga   2880
atccgccacc ggccccagga gcagctgcgc ttgcgcattg gcatccacac aggacctgtg   2940
tgtgctggag tggtgggact gaagatgccc cgttactgtc tctttgggga tacagtcaac   3000
acagcctcaa gaatggagtc taatggggaa gccctgaaga tccacttgtc ttctgagacc   3060
aaggctgtcc tggaggagtt tggtggtttc gagctggagc ttcgagggga tgtagaaatg   3120
aagggcaaag gcaaggttcg gacctactgg ctccttgggg agagggggag tagcacccga   3180
ggc                                                                 3183
```

<210> SEQ ID NO 19
<211> LENGTH: 1061
<212> TYPE: PRT
<213> ORGANISM: Homo sapiens

<400> SEQUENCE: 19

```
Met Pro Gly Pro Arg Pro Ala Gly Ser Arg Leu Arg Leu Leu Leu
1               5                   10                  15

Leu Leu Leu Pro Pro Leu Leu Leu Leu Arg Gly Ser His Ala
            20                  25                  30

Gly Asn Leu Thr Val Ala Val Val Leu Pro Leu Ala Asn Thr Ser Tyr
            35                  40                      45

Pro Trp Ser Trp Ala Arg Val Gly Pro Ala Val Glu Leu Ala Leu Ala
50                  55                      60

Gln Val Lys Ala Arg Pro Asp Leu Leu Pro Gly Trp Thr Val Arg Thr
65                  70                  75                  80

Val Leu Gly Ser Ser Glu Asn Ala Leu Gly Val Cys Ser Asp Thr Ala
                85                  90                  95

Ala Pro Leu Ala Ala Val Asp Leu Lys Trp Glu His Asn Pro Ala Val
            100                 105                 110

Phe Leu Gly Pro Gly Cys Val Tyr Ala Ala Pro Val Gly Arg Phe
            115                 120                 125

Thr Ala His Trp Arg Val Pro Leu Leu Thr Ala Gly Ala Pro Ala Leu
            130                 135                 140

Gly Phe Gly Val Lys Asp Glu Tyr Ala Leu Thr Thr Arg Ala Gly Pro
145                 150                 155                 160

Ser Tyr Ala Lys Leu Gly Asp Phe Val Ala Leu His Arg Leu
                165                 170                 175

Gly Trp Glu Arg Gln Ala Leu Met Leu Tyr Ala Tyr Arg Pro Gly Asp
                180                 185                 190

Glu Glu His Cys Phe Phe Leu Val Glu Gly Leu Phe Met Arg Val Arg
                195                 200                 205

Asp Arg Leu Asn Ile Thr Val Asp His Leu Glu Phe Ala Glu Asp Asp
            210                 215                 220

Leu Ser His Tyr Thr Arg Leu Leu Arg Thr Met Pro Arg Lys Gly Arg
225                 230                 235                 240

Val Ile Tyr Ile Cys Ser Ser Pro Asp Ala Phe Arg Thr Leu Met Leu
                245                 250                 255

Leu Ala Leu Glu Ala Gly Leu Cys Gly Glu Asp Tyr Val Phe Phe His
            260                 265                 270

Leu Asp Ile Phe Gly Gln Ser Leu Gln Gly Gly Gln Gly Pro Ala Pro
            275                 280                 285

Arg Arg Pro Trp Glu Arg Gly Asp Gly Gln Asp Val Ser Ala Arg Gln
290                 295                 300

Ala Phe Gln Ala Ala Lys Ile Ile Thr Tyr Lys Asp Pro Asp Asn Pro
305                 310                 315                 320

Glu Tyr Leu Glu Phe Leu Lys Gln Leu Lys His Leu Ala Tyr Glu Gln
                325                 330                 335

Phe Asn Phe Thr Met Glu Asp Gly Leu Val Asn Thr Ile Pro Ala Ser
            340                 345                 350

Phe His Asp Gly Leu Leu Leu Tyr Ile Gln Ala Val Thr Glu Thr Leu
            355                 360                 365

Ala His Gly Gly Thr Val Thr Asp Gly Glu Asn Ile Thr Gln Arg Met
```

```
              370                 375                 380
Trp Asn Arg Ser Phe Gln Gly Val Thr Gly Tyr Leu Lys Ile Asp Ser
385                 390                 395                 400

Ser Gly Asp Arg Glu Thr Asp Phe Ser Leu Trp Asp Met Asp Pro Glu
                405                 410                 415

Asn Gly Ala Phe Arg Val Val Leu Asn Tyr Asn Gly Thr Ser Gln Glu
                420                 425                 430

Leu Val Ala Val Ser Gly Arg Lys Leu Asn Trp Pro Leu Gly Tyr Pro
                435                 440                 445

Pro Pro Asp Ile Pro Lys Cys Gly Phe Asp Asn Glu Asp Pro Ala Cys
            450                 455                 460

Asn Gln Asp His Leu Ser Thr Leu Glu Val Leu Ala Leu Val Gly Ser
465                 470                 475                 480

Leu Ser Leu Leu Gly Ile Leu Ile Val Ser Phe Phe Ile Tyr Arg Lys
                485                 490                 495

Met Gln Leu Glu Lys Glu Leu Ala Ser Glu Leu Trp Arg Val Arg Trp
                500                 505                 510

Glu Asp Val Glu Pro Ser Ser Leu Glu Arg His Leu Arg Ser Ala Gly
                515                 520                 525

Ser Arg Leu Thr Leu Ser Gly Arg Gly Ser Asn Tyr Gly Ser Leu Leu
530                 535                 540

Thr Thr Glu Gly Gln Phe Gln Val Phe Ala Lys Thr Ala Tyr Tyr Lys
545                 550                 555                 560

Gly Asn Leu Val Ala Val Lys Arg Val Asn Arg Lys Arg Ile Glu Leu
                565                 570                 575

Thr Arg Lys Val Leu Phe Glu Leu Lys His Met Arg Asp Val Gln Asn
                580                 585                 590

Glu His Leu Thr Arg Phe Val Gly Ala Cys Thr Asp Pro Pro Asn Ile
                595                 600                 605

Cys Ile Leu Thr Glu Tyr Cys Pro Arg Gly Ser Leu Gln Asp Ile Leu
            610                 615                 620

Glu Asn Glu Ser Ile Thr Leu Asp Trp Met Phe Arg Tyr Ser Leu Thr
625                 630                 635                 640

Asn Asp Ile Val Lys Gly Met Leu Phe Leu His Asn Gly Ala Ile Cys
                645                 650                 655

Ser His Gly Asn Leu Lys Ser Ser Asn Cys Val Val Asp Gly Arg Phe
                660                 665                 670

Val Leu Lys Ile Thr Asp Tyr Gly Leu Glu Ser Phe Arg Asp Leu Asp
                675                 680                 685

Pro Glu Gln Gly His Thr Val Tyr Ala Lys Lys Leu Trp Thr Ala Pro
            690                 695                 700

Glu Leu Leu Arg Met Ala Ser Pro Pro Val Arg Gly Ser Gln Ala Gly
705                 710                 715                 720

Asp Val Tyr Ser Phe Gly Ile Ile Leu Gln Glu Ile Ala Leu Arg Ser
                725                 730                 735

Gly Val Phe His Val Glu Gly Leu Asp Leu Ser Pro Lys Glu Ile Ile
                740                 745                 750

Glu Arg Val Thr Arg Gly Glu Gln Pro Phe Arg Pro Ser Leu Ala
                755                 760                 765

Leu Gln Ser His Leu Glu Glu Leu Gly Leu Leu Met Gln Arg Cys Trp
            770                 775                 780

Ala Glu Asp Pro Gln Glu Arg Pro Pro Phe Gln Gln Ile Arg Leu Thr
785                 790                 795                 800
```

```
Leu Arg Lys Phe Asn Arg Glu Asn Ser Ser Asn Ile Leu Asp Asn Leu
            805                 810                 815

Leu Ser Arg Met Glu Gln Tyr Ala Asn Asn Leu Glu Glu Leu Val Glu
        820                 825                 830

Glu Arg Thr Gln Ala Tyr Leu Glu Glu Lys Arg Lys Ala Glu Ala Leu
    835                 840                 845

Leu Tyr Gln Ile Leu Pro His Ser Val Ala Glu Gln Leu Lys Arg Gly
850                 855                 860

Glu Thr Val Gln Ala Glu Ala Phe Asp Ser Val Thr Ile Tyr Phe Ser
865                 870                 875                 880

Asp Ile Val Gly Phe Thr Ala Leu Ser Ala Glu Ser Thr Pro Met Gln
                885                 890                 895

Val Val Thr Leu Leu Asn Asp Leu Tyr Thr Cys Phe Asp Ala Val Ile
            900                 905                 910

Asp Asn Phe Asp Val Tyr Lys Val Glu Thr Ile Gly Asp Ala Tyr Met
        915                 920                 925

Val Val Ser Gly Leu Pro Val Arg Asn Gly Arg Leu His Ala Cys Glu
    930                 935                 940

Val Ala Arg Met Ala Leu Ala Leu Leu Asp Ala Val Arg Ser Phe Arg
945                 950                 955                 960

Ile Arg His Arg Pro Gln Glu Gln Leu Arg Leu Arg Ile Gly Ile His
                965                 970                 975

Thr Gly Pro Val Cys Ala Gly Val Val Gly Leu Lys Met Pro Arg Tyr
            980                 985                 990

Cys Leu Phe Gly Asp Thr Val Asn  Thr Ala Ser Arg Met  Glu Ser Asn
            995                 1000                 1005

Gly Glu  Ala Leu Lys Ile His  Leu Ser Ser Glu Thr  Lys Ala Val
    1010                 1015                 1020

Leu Glu  Glu Phe Gly Gly Phe  Glu Leu Glu Leu Arg  Gly Asp Val
    1025                 1030                 1035

Glu Met  Lys Gly Lys Gly Lys  Val Arg Thr Tyr Trp  Leu Leu Gly
    1040                 1045                 1050

Glu Arg  Gly Ser Ser Thr Arg  Gly
    1055                 1060

<210> SEQ ID NO 20
<211> LENGTH: 4016
<212> TYPE: DNA
<213> ORGANISM: Rattus norvegicus

<400> SEQUENCE: 20 ccctttctt cttcctagga accagaccgt cctctccttc cctcgctctc caccgactcc      60
cttcggtgct gtgcttgctc ccacctgctc tgaagcgctc tccgctctcg gacgctccca    120
atttagcgct cctgctcgac ggccgaaccg tcgcagcctc cgcaggcagc gtgccctcgg    180
ggttgcggct tcaacccacc ccagcttcct ccctcgctac gactcgggcg ccctggacgt    240
tcgaccctcg ccgctgagcc cgaggatggc gagcagacca tggtgacagc gctgccggt     300 cgctgcactc gctgaggcca tgccgggctc ccgacgcgtc cgtccgcgcc taagggcgct    360
gctgctgctg ccgccgcttc tgctactccg gggcggccac gcgagcgacc tgaccgtggc    420
tgtggtgctg ccgctgacca acacctcgta cccgtggtcc tgggcgcgtg tagggccggc    480
cgtggaactg gctctcgcgc gggtgaaggc tcggccggac ttgctgccgg ttgacggt     540 ccgcatggtg ctgggcagca gtgagaacgc ggcgggcgtc tgctcggaca ccgccgcacc    600
```

```
gctggccgcg gtggacctca agtgggagca cagccccgcg gtgttcctgg gccccggctg    660
cgtctactcc gctgccccgg tggggcgctt caccgcgcac tggcgggtgc cgctgctgac    720
cgccggcgcc ccggctctgg gcatcggggt caaggatgag tatgcgctaa ccacccgcac    780
aggacccagc catgtcaagc tgggcgattt cgtgacggcg ctgcatcgac ggctgggctg    840
ggagcaccag gcgctggtgc tctatgcaga tcggctgggc gacgaccggc cttgcttctt    900
catagtggag gggctgtaca tgcgggtgcg tgaacgcctc aacatcacag tgaatcacca    960
ggagttcgtc gagggcgacc cggaccacta ccccaagcta ctgcgggccg tgcggcgaaa   1020
gggcagagtt atctacatct gcagttctcc ggatgccttc aggaatctga tgcttctggc   1080
cctgaacgct ggcctgactg gggaggacta tgttttcttc cacctggatg tgtttgggca   1140
aagccttaag agtgctcagg gccttgttcc ccagaaaccc tgggaaagag gagatgggca   1200
ggacaggagt gcccgccaag cctttcaggc tgccaaaatt attacttaca aagagcctga   1260
taatcctgag tacttggaat tcctgaagca gctgaaactc ttggctgaca agaagttcaa   1320
cttcaccgtg gaggatggcc tgaagaatat catcccagcc tccttccacg acgggctcct   1380
gctctatgtc caggcagtga cagagactct ggcacacggg gaactgtca cagatggaga   1440 gaacatcact cagcggatgt ggaaccgaag cttccaaggt gtgacaggat acccgaaaat   1500
tgatagaaac ggagatcggg acaccgattt ctctctctgg gatatggatc cagagacggg   1560
tgccttcagg gttgtcctga actataatgg tacttcccag gagctaatgg ctgtgtcaga   1620
acacaaatta tactggcctc tgggatatcc acctcctgac gtccctaaat gtggctttga   1680
caatgaggac ccagcctgca accaagacca cttttccaca ctggaggttc tggctttggt   1740
gggcagcctc tctctgatta gctttctgat tgtgtctttc ttcatataca ggaagatgca   1800
gctggaaaag gagctggtct cagagttgtg gcgggtgcgc tgggaggact gcagcccag   1860 cagcctggag aggcaccttc ggagcgctgg cagccggctg accctgagtg ggcgaggctc   1920
caattatggc tccctgctaa ccaccgaggg ccagttccaa gtctttgcca agacagcata   1980
ctataagggc aaccttgtgg ctgtgaaacg tgtgaaccgg aaacgcattg agttgacacg   2040
aaaagtcctg tttgaactta acatatgcg ggatgtgcag aatgaccact tgacaagatt   2100
tgtgggtgct tgtaccgacc ccccaacat ctgtatcctc acagagtact gtccccgtgg   2160
aagcctacag gacattctag agaatgagag tatcaccctg gactgatgt ttcggtactc   2220 gctcaccaat gacattgtca agggaatgct cttcctacac aatggggcca tttgttccca   2280
tgggaacctc aagtcatcca actgtgtggt agacgggcgc ttcgtgttaa agatcacaga   2340
ctacggtctt gagagcttca gagacccgga gccagagcaa ggacacaccc tctttgccaa   2400
aaaattgtgg acggcacctg agctcctgcg aatggcttcg ccacctgccc gtggctccca   2460
agctggggat gtgtacagct ttggtatcat cctgcaggag attgccctaa gaagtggggt   2520
cttctatgtg gaaggttgg acctcagccc aaaagagatc attgagcgtg tgactcgggg   2580
tgagcagccc ccattccgac cctccatgga tctgcagagc cacctggagg aactggggca   2640
gctgatgcag cggtgctggg cagaggaccc acaggagcgg ccacccttc agcagatccg   2700 cctggcgctc cgcaagttca caaggagaa cagcagcaac atcctggaca acctgctgtc   2760
acgcatggag cagtatgcta acaacctgga ggaactggta gaggagagaa cacaagctta   2820
tctggaggag aagcgcaaag ctgaggcctt gctttaccag attctgcctc actccgtggc   2880
tgagcagctg aagagaggcg agacagtcca ggctgaggcc tttgatagtg ttaccatcta   2940
```

```
cttcagtgat attgtgggct ttacagctct ttcagcagaa agcacaccca tgcaggtggt    3000
gactctgctc aatgatctgt acacctgttt tgatgctgtc atagacaact ttgatgtgta    3060
caaggtggag accattggtg atgcttacat ggtggtgtca gggctcccag tgcggaatgg    3120
acaactccac gcccgagagg tggcccgaat ggcacttgca ctactggatg ctgtgcgctc    3180
cttccgcatc cgccataggc cccaggaaca gctgcgcttg cgcattggca tccacacagg    3240
tcctgtgtgt gctggtgtgg tagggctaaa gatgcccga tactgcctct ttggagacac    3300
agtcaacaca gcttcaagaa tggagtctaa tggagaagcc ctcaagatcc acttgtcttc    3360
agagaccaag gctgtgctgg aagagttcga tggtttcgag ctggagctcc gaggggatgt    3420
ggaaatgaag ggcaaaggca aggttcggac ctattggctc ctgggggagc ggggatgtag    3480
cactcgaggc tgacctactg ccctgctgtt ccttgtcacc cctcctccct gtgccagagg    3540
tgacagaggt gtccagcttc cacctctccc acagcagccc agccactgtg gaaggattag    3600
ggacctgacc agcacagtca ccagatgtga cctctgagag aggatggaga tggtggggac    3660
tgcaggggac acctaagttt gtaggactga ctgaaacaca cagtccctcc catggcaccc    3720
ttgtggcaca catgcccagt cccacccta ctctgctgcc tagattggga cagcgattcc    3780
ttctctgccc tcaacttagc tccactgtga cttataggga gggaattgcc acctgaagga    3840
aacagaaaga ggttagagtt tgcaggaggc aggcagtcct gtgtcacaaa tactccctc    3900 acttccagcc caccacctgc cccacagact ttggacacag ctcactgagg agaagagaag    3960
ctgccggtta ccttgcttct cctgtgaacc aaaccattaa agtctttatt cctgtg        4016
```